(12) United States Patent
Frey et al.

(10) Patent No.: US 10,653,454 B2
(45) Date of Patent: May 19, 2020

(54) SPINAL FIXATION SYSTEMS

(71) Applicant: Mighty Oak Medical, Inc., Englewood, CO (US)

(72) Inventors: George Frey, Englewood, CO (US); Gregory Kana, Golden, CO (US)

( * ) Notice: Subject to any disclaimer, the term of this patent is extended or adjusted under 35 U.S.C. 154(b) by 212 days.

(21) Appl. No.: 15/985,373

(22) Filed: May 21, 2018

(65) Prior Publication Data

US 2018/0280061 A1 Oct. 4, 2018

Related U.S. Application Data

(63) Continuation of application No. 15/675,104, filed on Aug. 11, 2017, which is a continuation-in-part of (Continued)

(51) Int. Cl.
*A61B 17/00* (2006.01)
*A61B 17/17* (2006.01)
(Continued)

(52) U.S. Cl.
CPC .......... *A61B 17/7032* (2013.01); *A61B 17/17* (2013.01); *A61B 17/1703* (2013.01);
(Continued)

(58) Field of Classification Search
CPC . A61B 17/7032; A61B 17/17; A61B 17/1703; A61B 17/1732; A61B 17/8625;
(Continued)

(56) References Cited

U.S. PATENT DOCUMENTS 3,151,392 A 10/1967 Chambers
5,092,866 A 3/1992 Breard et al.
(Continued)

FOREIGN PATENT DOCUMENTS

CA 2736525 3/2010
CA 2862341 8/2013
(Continued)

OTHER PUBLICATIONS

Official Action with English Translation for Russia Patent Application No. 2014143528/14, dated Jan. 13, 2017 8 pages.
(Continued)

*Primary Examiner* — Pedro Philogene
(74) *Attorney, Agent, or Firm* — FisherBroyles, LLP; Ian R. Walsworth

(57) ABSTRACT

The present disclosure includes fixation devices that comprise one or more porous elements or fenestrations to aid in osteo-integration of the fixation device. These fixation devices may be additively manufactured using biocompatible materials such that the solid and porous aspects of the screw are fused together into a single construct. Spinal stabilization systems are also disclosed having spanning portions extending between and securable to pedicle screw assemblies, the spanning portions have stiffness characteristics that may be variable or selectively adjustable, and/or have non-linear behavior with respect to force versus distortion. Additionally, the systems may utilize a plurality of spanning portions in which two or more of the spanning portions have different stiffness characteristics. Methods for fabricating and using the foregoing devices are also described herein.

18 Claims, 26 Drawing Sheets

Related U.S. Application Data application No. 15/416,975, filed on Jan. 26, 2017, now Pat. No. 9,987,024, and a continuation-in-part of application No. 14/830,523, filed on Aug. 19, 2015, now abandoned, which is a continuation of application No. 12/172,996, filed on Jul. 14, 2008, now abandoned.

(60) Provisional application No. 62/373,855, filed on Aug. 11, 2016, provisional application No. 60/959,456, filed on Jul. 13, 2007.

(51) Int. Cl.

| | | |
|---|---|---|
| *A61B 17/34* | (2006.01) | |
| *A61B 17/70* | (2006.01) | |
| *A61B 17/86* | (2006.01) | |
| *A61B 17/84* | (2006.01) | |
| *A61B 34/10* | (2016.01) | |
| *A61B 34/20* | (2016.01) | |
| *A61F 2/30* | (2006.01) | |
| *A61F 2/44* | (2006.01) | |
| *A61F 2/46* | (2006.01) | |
| *B33Y 80/00* | (2015.01) | |
| *G09B 23/30* | (2006.01) | |
| *A61B 17/88* | (2006.01) | |
| *A61B 17/56* | (2006.01) | |

(52) U.S. Cl.
CPC ........ *A61B 17/1732* (2013.01); *A61B 17/864* (2013.01); *A61B 17/866* (2013.01); *A61B 17/8625* (2013.01); *A61B 17/88* (2013.01); *A61B 34/10* (2016.02); *A61F 2/44* (2013.01); *A61F 2/4611* (2013.01); *B33Y 80/00* (2014.12); *G09B 23/30* (2013.01); *A61B 34/20* (2016.02); *A61B 2017/00526* (2013.01); *A61B 2017/3447* (2013.01); *A61B 2017/561* (2013.01); *A61B 2017/8655* (2013.01); *A61B 2034/102* (2016.02); *A61B 2034/105* (2016.02); *A61B 2034/107* (2016.02); *A61B 2034/108* (2016.02); *A61F 2/30965* (2013.01); *A61F 2/4405* (2013.01); *A61F 2002/30948* (2013.01); *A61F 2002/30952* (2013.01); *A61F 2002/4687* (2013.01); *A61F 2310/00017* (2013.01); *A61F 2310/00023* (2013.01); *A61F 2310/00029* (2013.01); *A61F 2310/00047* (2013.01); *A61F 2310/00059* (2013.01)

(58) Field of Classification Search
CPC ..... A61B 17/864; A61B 17/866; A61B 17/88; A61B 34/10; A61B 34/20; A61B 2034/102; A61B 2034/105; A61B 2034/108; A61B 2017/00526; A61B 2017/3447; A61B 2017/561; A61B 2017/8655; B33Y 80/00; A61F 2/44; A61F 2/4611; A61F 2/30965; A61F 2/4405; A61F 2002/30948; A61F 2002/30952; A61F 2002/4687; A61F 2310/00017; A61F 2310/00023; A61F 2310/00029; A61F 2310/00047; A61F 2310/00059; G09B 23/30
USPC ................ 606/246–279, 300–328
See application file for complete search history.

(56) References Cited

U.S. PATENT DOCUMENTS

| | | |
|---|---|---|
| 5,129,904 A | 7/1992 | Illi |
| 5,201,734 A | 4/1993 | Cozard et al. |
| 5,291,901 A | 3/1994 | Graf |
| 5,360,448 A | 11/1994 | Thramann |
| 5,387,213 A | 1/1995 | Breard et al. |
| D359,557 S | 6/1995 | Hayes |
| 5,490,409 A | 2/1996 | Weber |
| 5,527,312 A | 6/1996 | Ray |
| 5,562,737 A | 10/1996 | Graf |
| 5,569,246 A | 10/1996 | Ojima et al. |
| 5,591,233 A | 1/1997 | Kelman et al. |
| 5,725,581 A | 3/1998 | Branemark |
| D403,066 S | 12/1998 | DeFonzo |
| 5,865,846 A | 2/1999 | Bryan et al. |
| RE36,221 E | 6/1999 | Breard et al. |
| D412,032 S | 7/1999 | Mikula-Curtis et al. |
| 5,961,516 A | 10/1999 | Graf |
| 5,993,453 A | 11/1999 | Bullara et al. |
| 6,006,581 A | 12/1999 | Holmes |
| D420,132 S | 2/2000 | Bucholz et al. |
| 6,030,401 A | 2/2000 | Marino |
| 6,035,691 A | 3/2000 | Lin et al. |
| 6,048,343 A | 4/2000 | Mathis et al. |
| 6,063,088 A | 5/2000 | Winslow |
| D428,989 S | 8/2000 | Segemark et al. |
| 6,113,602 A | 9/2000 | Sand |
| 6,142,998 A | 11/2000 | Smith et al. |
| 6,221,077 B1 | 4/2001 | Rinner et al. |
| 6,290,724 B1 | 9/2001 | Marino |
| 6,309,395 B1 | 10/2001 | Smith et al. |
| 6,328,738 B1 | 12/2001 | Suddaby |
| 6,364,880 B1 | 4/2002 | Michelson |
| 6,402,750 B1 | 6/2002 | Atkinson et al. |
| 6,445,211 B1 | 9/2002 | Saripella |
| 6,644,087 B1 | 11/2003 | Ralph et al. |
| 6,663,633 B1 | 12/2003 | Pierson, III |
| 6,711,432 B1 | 3/2004 | Krause et al. |
| 6,719,795 B1 | 4/2004 | Cornwall et al. |
| 6,755,839 B2 | 6/2004 | Van Hoeck et al. |
| 6,835,207 B2 | 12/2004 | Zacouto et al. |
| 7,014,640 B2 | 3/2006 | Kemppanien et al. |
| 7,025,769 B1 | 4/2006 | Ferree |
| 7,066,957 B2 | 6/2006 | Graf |
| 7,077,864 B2 | 7/2006 | Bryd, III et al. |
| D532,515 S | 11/2006 | Buttler et al. |
| D533,664 S | 12/2006 | Butler et al. |
| 7,207,992 B2 | 4/2007 | Ritland |
| 7,235,076 B2 | 6/2007 | Pacheco |
| 7,288,093 B2 | 10/2007 | Michelson |
| 7,291,150 B2 | 11/2007 | Graf |
| 7,341,590 B2 | 3/2008 | Ferree |
| 7,387,643 B2 | 6/2008 | Michelson |
| 7,406,775 B2 | 8/2008 | Funk et al. |
| 7,454,939 B2 | 11/2008 | Garner et al. |
| 7,491,180 B2 | 2/2009 | Pacheco |
| 7,537,664 B2 | 5/2009 | Oneill et al. |
| 7,559,931 B2 | 7/2009 | Stone |
| 7,578,851 B2 | 8/2009 | Dong et al. |
| 7,623,902 B2 | 11/2009 | Pacheco |
| D606,195 S | 12/2009 | Eisen et al. |
| 7,658,610 B2 | 2/2010 | Knopp |
| D618,796 S | 6/2010 | Cantu et al. |
| 7,844,356 B2 | 11/2010 | Matov et al. |
| 7,854,752 B2 | 12/2010 | Colleran et al. |
| 7,955,355 B2 | 6/2011 | Cin |
| 7,957,824 B2 | 6/2011 | Boronvinskih et al. |
| 7,957,831 B2 | 6/2011 | Isaacs |
| 7,967,868 B2 | 6/2011 | White et al. |
| 8,057,482 B2 | 11/2011 | Stone et al. |
| 8,070,752 B2 | 12/2011 | Metzger et al. |
| 8,092,465 B2 | 1/2012 | Metzger et al. |
| 8,118,815 B2 | 2/2012 | van der Walt |
| 8,159,753 B2 | 4/2012 | Ojeda et al. |
| 8,167,884 B2 | 5/2012 | Pacheco |
| 8,175,683 B2 | 5/2012 | Roose |
| 8,206,396 B2 | 6/2012 | Trabish |
| 8,214,014 B2 | 7/2012 | Pacheco |
| 8,236,006 B2 | 8/2012 | Hamada |
| 8,241,293 B2 | 8/2012 | Stone et al. |
| 8,257,083 B2 | 9/2012 | Berckmans et al. |
| D669,176 S | 10/2012 | Frey |

(56) References Cited

U.S. PATENT DOCUMENTS

| | | | |
|---|---|---|---|
| D669,984 S | 10/2012 | Cheney et al. | |
| 8,277,461 B2 | 10/2012 | Pacheco | |
| 8,282,646 B2 | 10/2012 | Schoenefeld et al. | |
| 8,292,967 B2 | 10/2012 | Brown et al. | |
| 8,298,235 B2 | 10/2012 | Grinberg et al. | |
| 8,298,237 B2 | 10/2012 | Schoenefeld et al. | |
| 8,298,242 B2 | 10/2012 | Justis et al. | |
| D672,038 S | 12/2012 | Frey | |
| 8,323,322 B2 | 12/2012 | Dawson et al. | |
| 8,328,849 B2* | 12/2012 | Nydegger | A61B 17/7022 606/254 |
| 8,357,111 B2 | 1/2013 | Caillouette et al. | |
| 8,377,066 B2 | 2/2013 | Katrana et al. | |
| 8,407,067 B2 | 3/2013 | Uthgenannt et al. | |
| 8,419,740 B2 | 4/2013 | Aram et al. | |
| D685,087 S | 6/2013 | Voic | |
| 8,460,303 B2 | 6/2013 | Park | |
| 8,475,505 B2 | 7/2013 | Nebosky et al. | |
| 8,480,679 B2 | 7/2013 | Park et al. | |
| 8,491,637 B2* | 7/2013 | Matthis | A61B 17/702 606/254 |
| 8,535,387 B2 | 9/2013 | Meridew et al. | |
| 8,540,719 B2 | 9/2013 | Peukert et al. | |
| 8,545,509 B2 | 10/2013 | Park et al. | |
| 8,549,888 B2 | 10/2013 | Isaacs | |
| 8,568,487 B2 | 10/2013 | Witt et al. | |
| 8,591,516 B2 | 11/2013 | Metzger et al. | |
| 8,603,180 B2 | 12/2013 | White et al. | |
| 8,607,603 B2 | 12/2013 | Justis et al. | |
| 8,608,748 B2 | 12/2013 | Metzger et al. | |
| 8,608,749 B2 | 12/2013 | Meridew et al. | |
| 8,632,547 B2 | 1/2014 | Maxson et al. | |
| 8,668,700 B2 | 3/2014 | Catanzarite | |
| 8,671,572 B2 | 3/2014 | Schlottig et al. | |
| D705,929 S | 5/2014 | Frey | |
| 8,721,651 B2 | 5/2014 | Loke et al. | |
| 8,758,357 B2 | 6/2014 | Frey | |
| 8,808,302 B2 | 8/2014 | Roose et al. | |
| 8,808,303 B2 | 8/2014 | Stemniski et al. | |
| 8,821,506 B2 | 9/2014 | Mitchell | |
| 8,858,561 B2 | 10/2014 | White et al. | |
| 8,864,769 B2 | 10/2014 | Stone et al. | |
| 8,870,889 B2 | 10/2014 | Frey | |
| D718,862 S | 12/2014 | Matheny | |
| D718,863 S | 12/2014 | Matheny | |
| D718,864 S | 12/2014 | Matheny | |
| 8,900,279 B2 | 12/2014 | Assell et al. | |
| 8,979,749 B2 | 3/2015 | Gorek et al. | |
| 8,979,911 B2 | 3/2015 | Martineau et al. | |
| 8,992,538 B2 | 3/2015 | Keefer | |
| D726,914 S | 4/2015 | Matheny | |
| 9,017,412 B2 | 4/2015 | Wolters et al. | |
| 9,044,285 B2 | 6/2015 | Harper | |
| 9,066,727 B2 | 6/2015 | Catanzarite et al. | |
| 9,066,816 B2 | 6/2015 | Allard et al. | |
| 9,113,971 B2 | 8/2015 | Metzger et al. | |
| D738,498 S | 9/2015 | Frey et al. | |
| 9,138,325 B2 | 9/2015 | Mouw | |
| 9,173,661 B2 | 11/2015 | Metzger et al. | |
| D745,671 S | 12/2015 | Frey et al. | |
| D745,672 S | 12/2015 | Frey et al. | |
| D745,673 S | 12/2015 | Frey et al. | |
| 9,198,678 B2 | 12/2015 | Frey et al. | |
| 9,216,045 B2 | 12/2015 | Martineau et al. | |
| 9,451,973 B2 | 9/2016 | Heilman et al. | |
| 9,456,901 B2 | 10/2016 | Jones et al. | |
| D775,335 S | 12/2016 | Frey et al. | |
| 9,642,633 B2 | 5/2017 | Frey et al. | |
| 9,649,160 B2 | 5/2017 | van der Walt et al. | |
| 9,662,157 B2 | 5/2017 | Schneider et al. | |
| 9,675,400 B2 | 6/2017 | Katrana et al. | |
| 9,737,339 B2 | 8/2017 | Copp et al. | |
| 9,814,497 B1 | 11/2017 | Al-Habib et al. | |
| 9,826,991 B2 | 11/2017 | Kaiser et al. | |
| 9,839,448 B2 | 12/2017 | Reckling et al. | |
| 9,848,922 B2 | 12/2017 | Tohmeh et al. | |
| 9,913,669 B1 | 3/2018 | Scholl et al. | |
| 9,949,843 B2 | 4/2018 | Reiley et al. | |
| 9,968,408 B1 | 5/2018 | Casey et al. | |
| 9,987,024 B2 | 6/2018 | Frey et al. | |
| 10,085,784 B2 | 10/2018 | Ono et al. | |
| 10,166,033 B2 | 1/2019 | Reiley et al. | |
| 2004/0097925 A1 | 5/2004 | Boehm et al. | |
| 2004/0144149 A1 | 7/2004 | Strippgen et al. | |
| 2004/0243481 A1 | 12/2004 | Bradbury et al. | |
| 2004/0267260 A1* | 12/2004 | Mack | A61B 17/7028 606/259 |
| 2005/0085815 A1 | 4/2005 | Harms et al. | |
| 2005/0148843 A1 | 7/2005 | Roose | |
| 2005/0177156 A1* | 8/2005 | Timm | A61B 17/7007 606/60 |
| 2005/0203514 A1 | 9/2005 | Jahng et al. | |
| 2005/0203519 A1 | 9/2005 | Harms et al. | |
| 2005/0262911 A1 | 12/2005 | Dankowicz et al. | |
| 2005/0288672 A1 | 12/2005 | Ferree | |
| 2006/0036323 A1 | 2/2006 | Carl et al. | |
| 2006/0058792 A1 | 3/2006 | Hynes | |
| 2006/0084986 A1 | 4/2006 | Grinberg et al. | |
| 2006/0095044 A1 | 5/2006 | Grady, Jr. et al. | |
| 2006/0149375 A1 | 7/2006 | Yuan et al. | |
| 2006/0241385 A1 | 10/2006 | Dietz | |
| 2006/0247637 A1* | 11/2006 | Colleran | A61B 17/7007 606/257 |
| 2006/0264935 A1 | 11/2006 | White | |
| 2007/0088359 A1 | 4/2007 | Woods et al. | |
| 2007/0093813 A1 | 4/2007 | Callahan, II et al. | |
| 2007/0093832 A1 | 4/2007 | Abdelgany | |
| 2007/0100341 A1 | 5/2007 | Reglos et al. | |
| 2007/0161985 A1 | 7/2007 | Demakas et al. | |
| 2007/0198014 A1 | 8/2007 | Graf et al. | |
| 2007/0227216 A1 | 10/2007 | Schalliol | |
| 2007/0288011 A1 | 12/2007 | Logan | |
| 2007/0288030 A1 | 12/2007 | Metzger et al. | |
| 2008/0086127 A1 | 4/2008 | Patterson et al. | |
| 2008/0114370 A1 | 5/2008 | Shoenefeld | |
| 2008/0161815 A1 | 7/2008 | Shoenefeld et al. | |
| 2008/0183214 A1 | 7/2008 | Copp et al. | |
| 2008/0255564 A1 | 10/2008 | Michelson | |
| 2008/0257363 A1 | 10/2008 | Schoenefeld et al. | |
| 2008/0275452 A1 | 11/2008 | Lang et al. | |
| 2008/0306552 A1 | 12/2008 | Winslow | |
| 2008/0312659 A1 | 12/2008 | Metzger et al. | |
| 2008/0319491 A1 | 12/2008 | Schoenefeld | |
| 2009/0048631 A1* | 2/2009 | Bhatnagar | A61B 17/7004 606/246 |
| 2009/0076555 A1 | 3/2009 | Lowry et al. | |
| 2009/0087276 A1 | 4/2009 | Rose | |
| 2009/0088674 A1 | 4/2009 | Caillouette et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0105760 A1 | 4/2009 | Frey | |
| 2009/0110498 A1 | 4/2009 | Park | |
| 2009/0138020 A1 | 5/2009 | Park et al. | |
| 2009/0187194 A1 | 7/2009 | Hamada | |
| 2009/0198277 A1 | 8/2009 | Gordon et al. | |
| 2009/0254093 A1 | 10/2009 | White et al. | |
| 2009/0270868 A1 | 10/2009 | Park et al. | |
| 2009/0326537 A1 | 12/2009 | Anderson | |
| 2010/0016984 A1 | 1/2010 | Trabish | |
| 2010/0049195 A1 | 2/2010 | Park et al. | |
| 2010/0082035 A1 | 4/2010 | Keefer | |
| 2010/0087829 A1 | 4/2010 | Metzger et al. | |
| 2010/0100193 A1 | 4/2010 | White | |
| 2010/0152782 A1 | 6/2010 | Stone et al. | |
| 2010/0191244 A1 | 7/2010 | White et al. | |
| 2010/0217270 A1 | 8/2010 | Polinski et al. | |
| 2010/0217336 A1 | 8/2010 | Crawford et al. | |
| 2010/0305700 A1 | 12/2010 | Ben-Arye et al. | |
| 2010/0324692 A1 | 12/2010 | Uthgenannt et al. | |
| 2011/0015636 A1 | 1/2011 | Katrana et al. | |
| 2011/0015639 A1 | 1/2011 | Metzger et al. | |
| 2011/0046735 A1 | 2/2011 | Metzger et al. | |

(56) References Cited

U.S. PATENT DOCUMENTS

| | | |
|---|---|---|
| 2011/0054478 A1 | 3/2011 | Vanasse et al. |
| 2011/0071533 A1 | 3/2011 | Metzger et al. |
| 2011/0093023 A1 | 4/2011 | Lee et al. |
| 2011/0093086 A1 | 4/2011 | Witt et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0213376 A1 | 9/2011 | Maxson et al. |
| 2011/0218545 A1 | 9/2011 | Catanzarite et al. |
| 2011/0224674 A1 | 9/2011 | White et al. |
| 2011/0288433 A1 | 11/2011 | Kelleher et al. |
| 2012/0041445 A1 | 2/2012 | Roose et al. |
| 2012/0130434 A1 | 5/2012 | Stemniski et al. |
| 2012/0150243 A9 | 6/2012 | Crawford et al. |
| 2012/0179259 A1 | 7/2012 | McDonough et al. |
| 2012/0215315 A1 | 8/2012 | Hochschuler et al. |
| 2012/0245587 A1 | 9/2012 | Fang |
| 2013/0006251 A1 | 1/2013 | Aram et al. |
| 2013/0053854 A1 | 2/2013 | Schoenefeld et al. |
| 2013/0110174 A1 | 5/2013 | Marik |
| 2013/0123850 A1 | 5/2013 | Schoenefeld et al. |
| 2014/0137618 A1 | 5/2014 | Isaacs |
| 2014/0379032 A1 | 12/2014 | Hennard |
| 2015/0047410 A1 | 2/2015 | Petit et al. |
| 2015/0119939 A1 | 4/2015 | Frey et al. |
| 2015/0127053 A1 | 5/2015 | Maruenda Paulino et al. |
| 2015/0201970 A1* | 7/2015 | Aferzon ............. A61B 17/7019 606/257 |
| 2015/0297249 A1 | 10/2015 | Catanzarite |
| 2016/0030067 A1 | 2/2016 | Frey et al. |
| 2016/0270802 A1 | 9/2016 | Fang et al. |
| 2017/0215857 A1 | 8/2017 | D'Urso |

FOREIGN PATENT DOCUMENTS

| | | |
|---|---|---|
| CN | 201275138 | 7/2009 |
| CN | 201404283 | 2/2010 |
| CN | 101390773 | 11/2010 |
| CN | 101953713 | 1/2011 |
| CN | 104306061 | 1/2015 |
| CN | 105078563 | 11/2015 |
| CN | 106175911 | 12/2016 |
| CN | 104224306 | 8/2017 |
| DE | 102013110699 | 4/2015 |
| DE | 202014011170 U1 | 4/2018 |
| EP | 2168507 | 3/2010 |
| EP | 2957244 | 12/2015 |
| EP | 2749235 | 8/2017 |
| EP | 3381382 | 10/2018 |
| FR | 3012030 | 12/2015 |
| FR | 3023655 | 4/2018 |
| GB | 2447702 | 9/2008 |
| JP | 10071157 | 3/1998 |
| JP | 2002531214 | 9/2002 |
| JP | 2005118569 | 5/2005 |
| JP | 2006528533 | 12/2006 |
| JP | 2007502692 | 2/2007 |
| JP | 2007510482 | 4/2007 |
| JP | 2012143379 | 8/2012 |
| JP | D1508406 | 10/2014 |
| WO | WO2004071314 | 8/2004 |
| WO | 200503710 | 4/2005 |
| WO | 2006039266 | 4/2006 |
| WO | 2006066053 | 6/2006 |
| WO | 2006079531 | 8/2006 |
| WO | 2007037920 | 4/2007 |
| WO | 2007145937 | 12/2007 |
| WO | 2008027549 | 3/2008 |
| WO | WO2009004625 | 1/2009 |
| WO | 2009035358 | 3/2009 |
| WO | WO2006017641 | 4/2009 |
| WO | WO2008157412 | 4/2009 |
| WO | 2009129063 | 10/2009 |
| WO | 2009105106 | 12/2009 |
| WO | WO2010033431 | 3/2010 |
| WO | 2010148103 | 12/2010 |
| WO | 2011041398 | 4/2011 |
| WO | 2011080260 | 7/2011 |
| WO | 2011106711 | 9/2011 |
| WO | 2011109260 | 9/2011 |
| WO | WO2012082164 | 6/2012 |
| WO | 2012152900 | 11/2012 |
| WO | 2013041618 | 3/2013 |
| WO | WO2013041618 | 3/2013 |
| WO | 2013104682 | 7/2013 |
| WO | WO2013169674 | 11/2013 |
| WO | WO2013173700 | 11/2013 |
| WO | WO2014070889 | 5/2014 |
| WO | 2014088801 | 6/2014 |
| WO | WO2014090908 | 6/2014 |
| WO | WO2014095853 | 6/2014 |
| WO | 2014143762 | 9/2014 |
| WO | WO2014198279 | 12/2014 |
| WO | WO2016148675 | 9/2016 |

OTHER PUBLICATIONS

International Search Report and Written Opinion for International (PCT) Patent Application No. PCT/US15/32356, dated Oct. 28, 2015 10 pages.
International Preliminary Report on Patentability for International (PCT) Patent Application No. PCT/US2015/032356, dated Dec. 15, 2016 7 pages.
International Search Report and Written Opinion for International (PCT) Patent Application No. PCT/US2016/056970, dated 10, 2017 13 pages.
International Search Report and Written Opinion for International (PCT) Patent Application No. PCT/US2014/041379, dated Oct. 28, 2014, 7 pages.
International Preliminary Report on Patentability for International (PCT) Patent Application No. PCT/US2014/041379, dated Dec. 17, 2015 6 pages.
Official Action for Canada Patent Application No. 2,914,005, dated Feb. 3, 2017 3 pages.
Official Action for U.S. Appl. No. 13/172,683, dated Sep. 10, 2013 7 pages.
Office Action for U.S. Appl. No. 13/172,683, dated Feb 24, 2014 10 pages.
Notice of Allowance for U.S. Appl. No. 13/172,683, dated Apr. 23, 2014 7 pages.
Notice of Allowance for U.S. Appl. No. 29/409,734, dated May 11, 2012 8 pages.
Notice of Allowance for U.S. Appl. No. 29/427,918, dated Oct. 15, 2012 9 pages.
Notice of Allowance for U.S. Appl. No. 19/432,668 dated Nov. 27, 2013 11 pages.
Notice of Allowance for U.S. Appl. No. 29/476,709, dated Nov. 6, 2015, 8 pages.
Notice of Allowance for U.S. Appl. No. 29/476,705, dated Oct. 7, 2015, 8 Pages.
Notice of Allowance for U.S. Appl. No. 29/476,699, dated Oct. 2, 2015, 8 pages.
Notice of Allowance for U.S. Appl. No. 29/496,231, dated Jul. 23, 2015 10 pages.
Notice of Allowance for U.S. Appl. No. 29/538,633, dated Jan. 6, 2016 10 pages.
Official Action for U.S. Appl. No. 13/841,069, dated Jul. 31, 2014 9 pages.
Notice of Allowance for U.S. Appl. No. 13/841,069, dated Sep. 18, 2014 7 pages.
Office Action for U.S. Appl. No. 14/298,634, dated Apr. 27, 2015, 8 pages.
Office Action for U.S. Appl. No. 14/298,634, dated Jul. 7, 2015 6 pages.

(56) References Cited

OTHER PUBLICATIONS

Notice of Allowance for U.S. Appl. No. 14/298,624, dated Oct. 7, 2015 7 pages.
Notice of Allowance for U.S. Appl. No. 14/883,299, dated Mar. 20, 2017 12 pages.
"Calculator for Designing Compression Springs," eFunda, Inc., first published online Sep. 25, 2000 per Wayback Machine, 2 pages, [retrieved from: http://www.efunda.com/designstandards/springs/calc_comp_designer.cfm].
Juvinall et al. "Fundamentals of Machine Component Design," Wiley, Dec. 2004, 4th edition, 5 pages [retrieved from: http://tocs.ulb.tu-darmstadt.de/178455539.pdf].
International Search Report and Written Opinion for International (PCT) Patent Application No. PCT/US08/08637 dated Oct. 20, 2009, 8 pages.
International Preliminary Report on Patentability for International (PCT) Patent Application No. PCT/US08/08637 dated Jan. 19, 2010, 6 pages.
Official Office Action for Australian Patent Application No. 52008276577 dated Nov. 2, 2012 5 pages.
Notice of Acceptance for Australia Patent Application No. 2008276577, dated Jan. 21, 2014 2 pages.
Official Action for Australia Patent Application No. 2014202363, dated Nov. 14, 2014 6 pages.
Official Action for Australia Patent Application No. 2014202363, dated Apr. 1, 2015 3 pages.
Official Action for Australia Patent Application No. 2014202363, dated Aug. 3, 2015 4 pages.
Official Action for Australia Patent Application No. 2014202363, dated Sep. 18, 2015 6 pages.
Official Action for Canada Patent Application No. 2,693,682, dated Jan. 21, 2014 2 pages.
Extended European Search Report for European Patent Application No. 08794499.7 dated Oct. 8, 2012, 13 pages.
Official Action for European Patent Application No. 08794499.7, dated Jul. 2, 2013 6 pages.
Notice of Allowance for European Patent Application No. 08794499.7 dated Mar. 19, 2014 6 pages.
Extended Search Report for European Patent Application No. 14180580.4, dated Oct. 15, 2015 9 pages.
Official Action (with English Translation) for Japanese Patent Application No. 2010-517004 dated Jan. 15, 2013 6 pages.
Official Action (with English Translation) for Japanese Patent Applicaiton No. 2010-517004 dated Oct. 11, 2013 4 pages.
Re-Examination Report with English Translation for Japan Patent Application No. 2010-517004, dated Apr. 1, 2014 2 pages.
Official Action with English Translation for Japan Patent Application No. 2010-517004, dated Dec. 5, 2014 4 pages.
Official Action for U.S. Appl. No. 12/172,996, dated Apr. 13, 2011 5 pages Restriction Requirement.
Official Action for U.S. Appl. No. 12/172,996, dated Jun. 9, 2011 10 pages.
Official Action for U.S. Appl. No. 12/172,996, dated Dec. 7, 2011 10 pages.
Official Action for U.S. Appl. No. 12/172,996, dated Sep. 25, 2014 11 pages.
Official Action for U.S. Appl. No. 12/172,996, dated May 21, 2015 11 pages.
Official Action for U.S. Appl. No. 14/478,744, dated Jul. 30, 3015 8 pages.
"Introducing IntelliSense Drill Technology®", McGinley Orthopaedic Innovations, 1 page, [captured Feb. 29, 2016 from: http://web.archive.org/web/20160229042028/http://www.mcginleyorthopaedicinnovations.come/index.php?/drill].

Brussel et al. "Medical Image-Based Design of an Individualized Surgical Guide for Pedicle Screw Insertion." 18th Annual International Conference of the IEEE Engineering in Medicine and Biology Society, Amsterdam 1996, pp. 225-226.
Dai et al. "Surgical treatment of the Osteoporotic spine with bone cement-injectable cannulated pedicle screw fixation: technical description and preliminary application in 43 patients," Clinics, Feb. 2015, vol. 70, No. 2, pp. 114-119.
Hong et al. "Binder-jetting 3D printing and alloy development of new biodegradable Fe—Mn—Ca/Mg alloys," Acta Biomaterialia, Nov. 2016, vol. 45, pp. 375-386 (Abstract Only) 4 pages.
Jakus et al. "Hyperelastic "bone": A highly versatile, growth factor-free, osteoregenerative, scalable, and surgically friendly biomaterial," Science Translational Medicine, Sep. 2016, vol. 8, No. 358, pp. 358ra127 (Abstract only) 5 pages.
Lu et al. "A novel computer-assisted drill guide template for lumbar pedicle screw placement: a cadaveric and clinical study." The International Journal of Medical Robotics and Computer Assisted Surgery, Jun. 2009, vol. 5, No. 2, pages 184-191. (Abstract only).
Lu et al. "A Noverl Patient-Specific Navigational Template for Cervical Pedicle Screw Placement," Spine, Dec. 15, 2009, vol. 34, No. 26, pp. E959-E966 (Abstract only).
Owen et al. "Rapid prototype patient-specific drill template for cervical pedicle screw placement." Computer Aided Surgery, Sep. 2007, vol. 12, No. 5, pp. 303-308 (Abstract Only).
Ryken et al. "Image-based drill templates for cervical pedicle screw placement Laboratory investigation," Journal of Neurosurgery, Jan. 2009, vol. 10, No. 1 (Abstract Only).
Yin et al. "Computer aid designed digital targeting template of pedicle of vertebral arch for atlantoaxial nailing," IT in Medicine & Education, 2009. ITIME '09. Aug. 14-16, 2009, vol. 1 (Abstract Only).
International Search Report and Written Opinion for International (PCT) Patent Application No. PCT/US11/42412 dated Nov. 8, 2011, 8 pages.
International Preliminary Report on Patentability for international (PCT) Patent Application No. PCT/US11/42412 dated Jan. 17, 2013, 7 pages.
Official Action for Australian Patent Application No. 2011276468 dated Apr. 10, 2013 3 pages.
Official Action for Canada Patent Application No. 2,802,094, dated Feb. 14, 2017, 4 pages.
Partial Search Report for European Patent Application No. 118041912, dated Jan. 20, 2015, 6 pages.
Extended Search Report for European Patent Application No. 11804191.2 dated May 7, 2015 8 pages.
Official Action for European Patent Application No. 11804191.2, dated Feb. 17, 2017 5 pages.
Official Action with English Translation for Japan Patent Application No. 2013-518663, dated May 12, 2015 4 pages.
Notice of Allowance with English Translation for Japan Patent Application No. 2013-518663 dated Dec. 8, 2015 4 pages.
International Search Report and Written Opinion for International (PCT) Patent Application No. PCT/US2013/036535, dated Jun. 26, 2013, 8 pages.
International Preliminary Report on Patentability for International (PCT) Patent Application No. PCT/US2013/036535, dated Oct. 30, 2014, 7 pages.
Official Action with English Translation for China Patent Application No. 201380030638.3, dated May 25, 2016 11 pages.
Official Action with English Translation for China Patent Application No. 2013800306383, dated Feb. 4, 2017 6 pages.
Extended Search Report for European Patent Application No. 13778164.7, dated Feb. 17, 2016 10 pages.
Notice of Allowance with English Translation for Japan Patent Application No. 2015-507078, dated Jan. 10, 2017 4 pages.

* cited by examiner

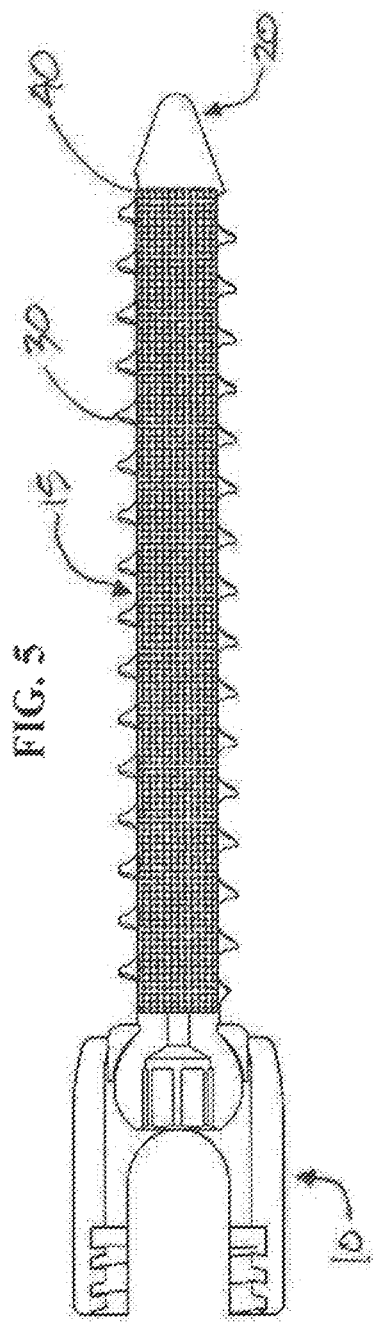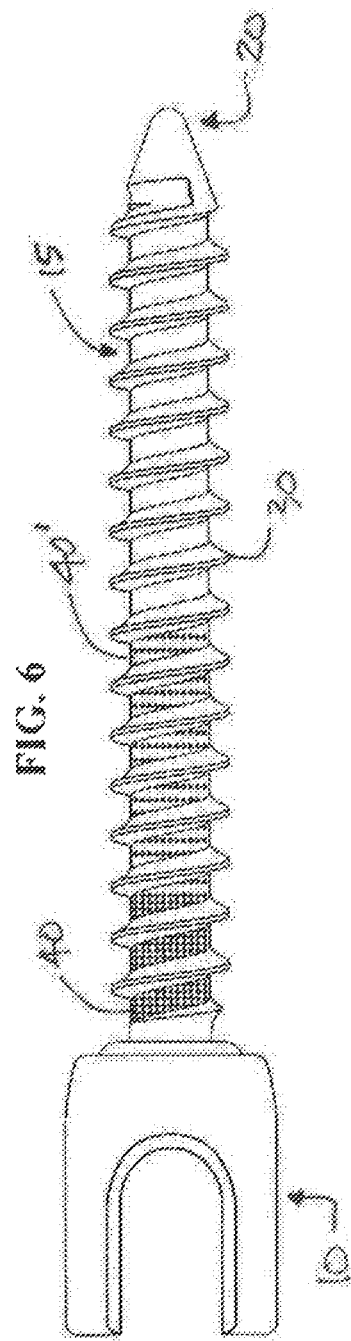

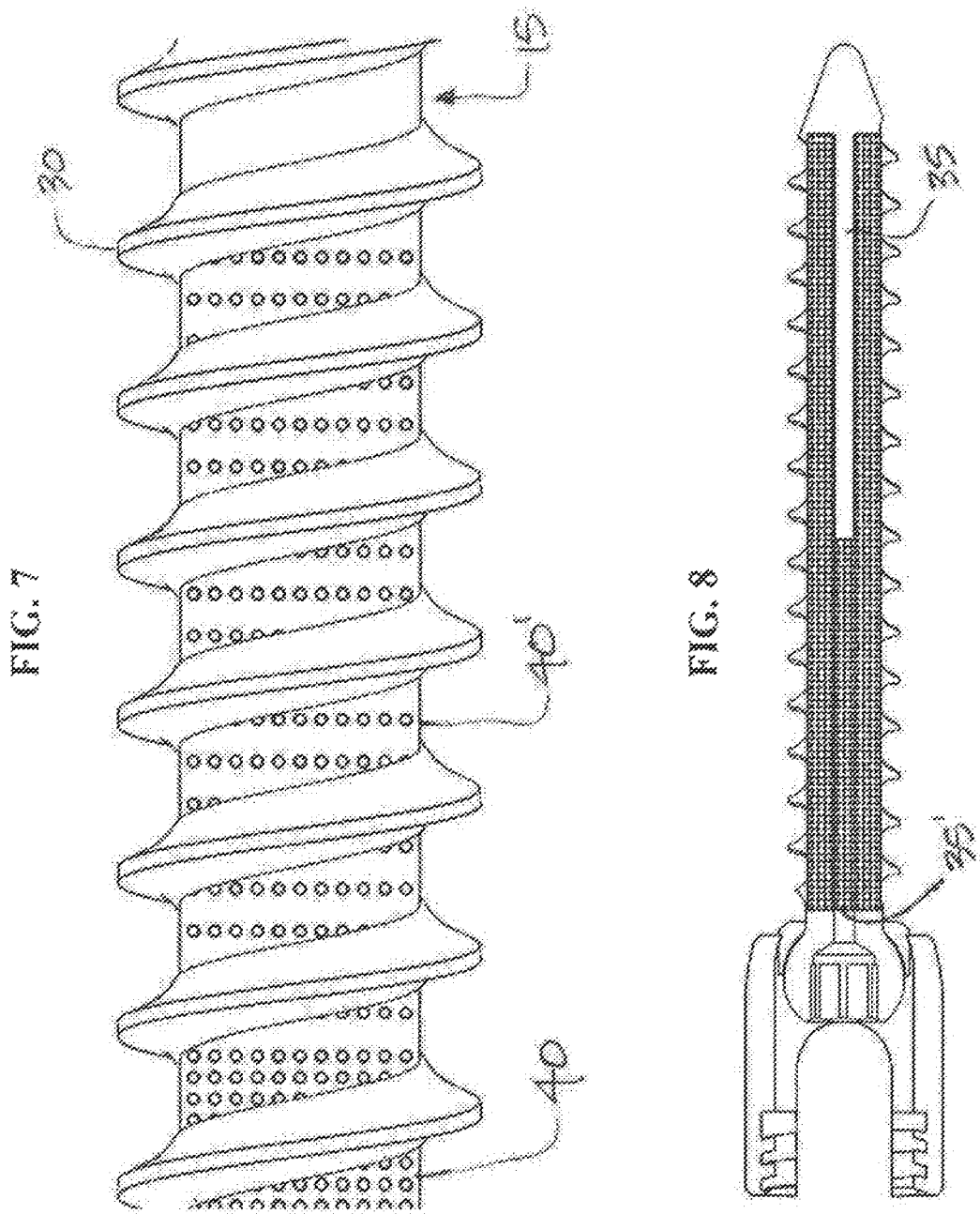

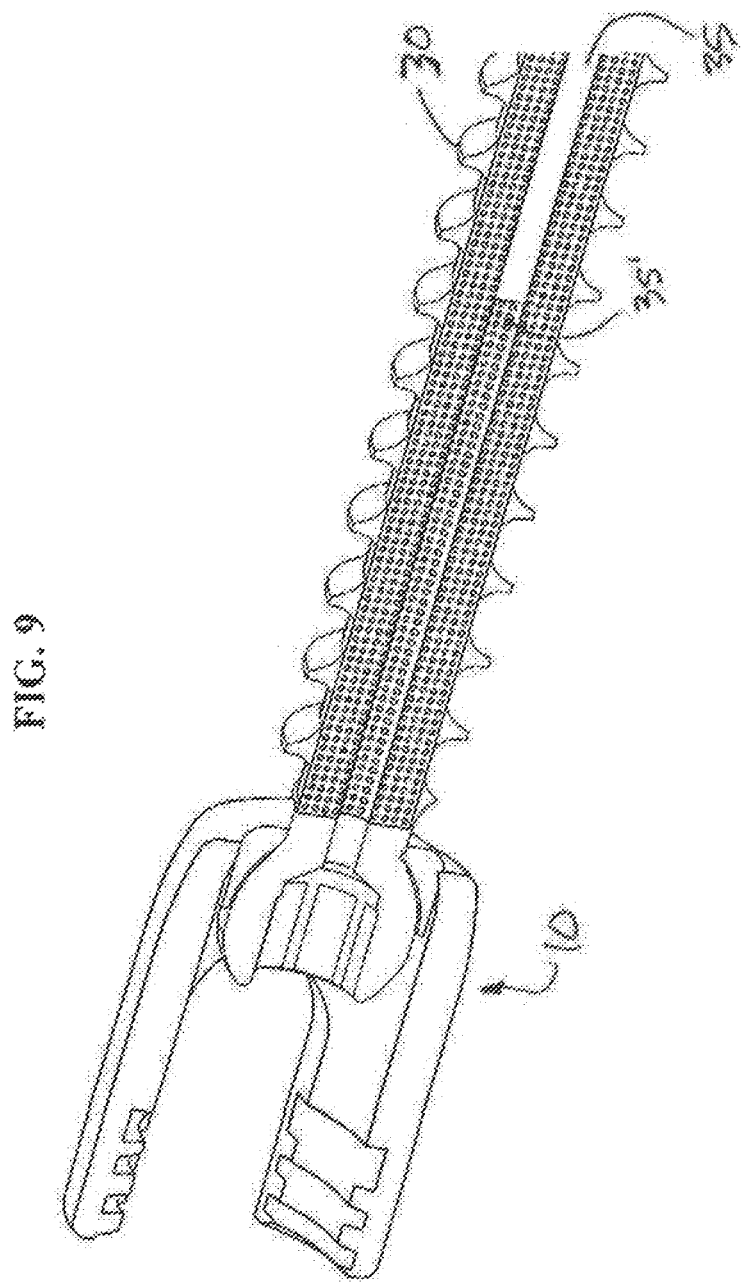

SPINAL FIXATION SYSTEMS

CROSS-REFERENCE TO RELATED APPLICATIONS

The present application is a continuation application and claims the benefit and priority of U.S. patent application Ser. No. 15/675,104, filed Aug. 11, 2017, which is a continuation-in-part of U.S. patent application Ser. No. 15/416,975, filed on Jan. 26, 2017, which which issued as U.S. Pat. No. 9,987,024 on Jun. 5, 2018, which claims the benefit of U.S. Provisional Application No. 62/373,855, filed Aug. 11, 2016.

This application is also a continuation in part and claims the benefit and priority of U.S. patent application Ser. No. 14/830,523 filed Aug. 19, 2015, which is a continuation of U.S. patent application Ser. No. 12/172,996 filed Jul. 14, 2008, now abandoned, which claims the benefit of U.S. Provisional Patent Application No. 60/959,456 filed Jul. 13, 2007. The entire disclosures of the prior applications are incorporated by reference.

FIELD OF THE INVENTION

The present disclosure relates to the field of medical devices generally. More specifically, the present disclosure relates to dynamic fixation and stabilization devices for use in spinal-related surgeries. Systems and methods for fabricating and using the foregoing devices are also disclosed herein.

BACKGROUND OF THE INVENTION

Individuals who suffer degenerative disc disease, natural spine deformations, a herniated disc, spine injuries or other spine disorders often require surgery on the affected region to relieve pain and prevent further injury. Such spinal surgeries may involve fixation of two or more adjacent vertebral bodies. For patients with varying degrees of degenerative disc disease and/or nerve compression with associated lower back pain, spinal fusion surgery or lumbar arthrodesis ("fusion") is commonly used to treat the degenerative disease. Fusion commonly involves distracting and/or decompressing one or more intervertebral spaces, followed by removing any associated facet joints or discs, and then joining or "fusing" two or more adjacent vertebra together. Fusion of vertebral bodies also commonly involves fixation of two or more adjacent vertebrae, which may be accomplished through introduction of rods or plates, and screws or other devices into a vertebral joint to join various portions of a vertebra to a corresponding portion on an adjacent vertebra. Given the complexities of surgical procedures, as well as anatomical variation between patients who receive surgical devices, it is often challenging to provide a device or implant that achieves the needs of a particular patient without completely customizing the device or implant for a single patient.

Many prior art fixation devices suffer from significant disadvantages, such as poor stability, poor flexibility, poor accuracy, difficulty in handling, lack of customized features, inability to combine with other materials, loss of fixation over time, subsidence and other disadvantages. Certain fixation devices also impair visibility and provide little or no ability for the operator to gauge depth or accuracy. These problems and shortcomings are even more noticeable for fixation devices used in surgical settings or which otherwise require precision.

In addition, fixation devices used in surgical settings can also suffer from further shortcomings. For example, pedicle screws are subject to relatively high failure rates, which is often attributed to a failure of the bone-screw interface. Screws for use in surgical settings may also be limited for use in only certain boney anatomies, or with only certain types of drilling apparatus, and may not be suitable for combination with other devices or materials.

Accordingly, there is a need for a fixation device that decreases the mean time for affixing the device to the desired location, enhances depth control, stability and accuracy, and which otherwise overcomes the disadvantages of the prior art. There is also need for a more customized fixation device, such as an orthopedic screw, which includes one or more porous elements or fenestrations to aid in osteo-integration when implanting the fixation device. The fixation device may be additively manufactured using biocompatible materials such that the solid and porous aspects of the device are fused together into a single solid construct, and potentially having the porous elements interdigitated within and around various solid elements of the device.

The prior art also fails to teach a system for creating a customized fixation device based on patient data, such as data derived from a patient's MRI or CT scan. For example, the availability of patient-specific data (for example, a vertebral body) may allow a surgeon to accommodate for subtle variations in the position and orientation of a screw or other fixation device to avoid particular boney anatomy, or irregularities in the positioning and alignment of the adjoining vertebral bodies. As another example, the use of patient data may also assist a surgeon in selecting a desired trajectory for a fixation device so as to avoid, for example, crossing the pedicle wall and violating the spinal canal during a spine-related procedure. The use of patient-specific data permits the surgeon to avoid these types of mistakes and may comprise specific orientation, end-stops/hard stops, or other safety related features to avoid over-torque or over-insertion of the fixation device. This data also permits the surgeon to quickly and efficiently locate and place devices with corresponding patient-contacting surface(s), while ensuring the fixation device is in the appropriate location and orientation.

Current spinal stabilization devices and systems typically involve the use of anchors secured with a plurality of vertebrae and sometimes span between the anchors. Such devices are often referred to by the portion of the vertebra to which the anchors secure. For instance, a laminar stabilization system utilizes anchors, typically hooks, secured with the lamina of a vertebra. As another example, a stabilization utilizing anchors in the form of a screw is often referred to as a pedicle screw system, as the screws themselves are driven into the pedicle portion of the vertebra. Generally speaking, the spanning member is the least considered part of this type of system. A surgeon's choices for spanning members are virtually limited to selecting either a rod or a bar, the length of the spanning member, and a cross-sectional dimension such as the rod's diameter. It should be noted that there are particularized types of rod a surgeon can select. Generally, however, these rods are limited in use to an entire system, and the deviation from the standard rod provided by these rods is not for mechanical behavior characteristics, instead being for cooperation with the other particularized features of a specific stabilization system.

Other than portions of the above discussion, the term "stabilization system" is meant to refer only to spinal stabilization systems that attach to one or more vertebrae in a manner that does not affect or interfere with the intervertebral space, nucleus, or annulus. Accordingly, laminar or pedicle systems or the like are each intended to be encompassed by the term "stabilization system." In general terms, a stabilization system is implanted through an open and retracted incision by securing at least one anchor on an inferior vertebra and at least one anchor on a superior vertebra. It should also be noted that the medical community is continuing to develop minimally invasive surgical techniques for implantation of such devices. Typically, a pair of anchors is secured with each of the vertebrae, and typically the vertebrae are adjacent. In some forms, the stabilization system may span three or more vertebrae and be secured with any two or more of the vertebrae.

Spanning members are then secured with the anchors. This commonly requires forcing rods into a yoke secured with each of the anchors. In some forms, the anchor and yoke are of a type referred to as "polyaxial" by their ability to pivot relative to each other so that a channel in the yoke for receiving the rod becomes aligned in an optimal orientation for receiving the rod. The spanning members are usually then secured in and with the yoke with a securement in the form of a cap that is received in an upper portion of the yoke channel.

The entire stabilization system is generally highly rigid. Once the rod is secured therein, the cap and the yoke frequently distort or deface the surface of the rod via the pressure exert to secure the rod therein. This prevents movement of the rod within (such as rotation) or relative to the yoke and anchor (such as longitudinal sliding). The rod itself is formed of a high modulus of elasticity metal, and its mechanical behavior displays little elasticity.

Stabilization systems have been developed to allow some motion in one or more directions. Generally, motion of a normal, healthy spine includes anterior-posterior flexure, lateral flexure, and rotation, or any combination of these. Due to disease, damage, or natural defect, the purpose of the stabilization system may vary. Depending on such purpose for the stabilization procedure utilizing the stabilization systems, motion in one or more directions may be preferred to a rigid system.

It is also known that there are medical detriments that can arise from full immobilization. For instance, it is know that a lack of pressure (i.e., stress, or weight) on bones can result in a decrease in density. An expression known as Wolf's law describes the benefits of pressure on bones or bone fragments as they are healing, benefits that can be negated by an overly rigid spinal stabilization system. It is also suspected that intervertebral structures may suffer from a lack of use resulting from rigid systems. Additionally, full immobilization can result in overstressing of adjacent areas, thus producing adjacent segment degeneration.

Accordingly, some stabilizations systems have been designed to allow the portion of the spine to which the system is secured to bend itself. For instance, the ends of a spanning member may be curved relative to each other due to motion in some directions, like a cylindrical rod being curved.

A complicated example of stabilization system permitting some bending motion is described in U.S. Pat. No. 5,961,516, to Graf. In simple terms, the system of the '516 patent includes anchors for respective vertebrae and a spanning structure connected with the anchors. The spanning structure includes a ball joint between two portions, and a "compressible" body acting as a shock absorber. The various components of the system of the '516 patent must clamp tightly and utilize friction in order to resist free movement. Over time, such friction results in wear to the components, which in turn may lead to reduced performance of the components and revision surgery, or fragments of the components being free in the patient's body. It is also known that implantation of an elastomeric/polymeric compressible member is difficult as the material is prone to release of polymeric byproducts and is prone to chemical and mechanical degradation.

Another direction of motion that ideally is accommodated is that which shifts the anchors themselves relatively and directly in line with the spanning structure. The '516 patent purports to provide a system that allows spinal motion in all directions, only the compressible member allows the spanning structure itself to shorten; additionally, the compressible member is not shown as being able to expand for the spanning structure being lengthened.

Once implanted, the stabilization systems are generally constant in their behavior characteristics, other than changes due to wearing of components or the like. To be specific, a surgeon may select a specific diameter for a rod to span between two anchors, and the diameter and material can be selected for their mechanical properties. The surgeon may also determine either a length of the rod or a distance between the anchors based on how the rod is secured with the anchors. However, the selection of the rod diameter is quantized as it is a specific size, and the surgeon is unable to adjust the exact diameter during a procedure other than to select from specific, predetermined diameters. Subsequent to the surgical procedure, the surgeon is unable to adjust the distance between the anchors without a further, revision surgical procedure, which would also be required if a surgeon were to determine a different diametrally-sized rod would be preferred (such as to increase or decrease the flexure of the spanning structure).

In the selection of the stabilization systems discussed, a surgeon is not provided with sufficient implant options for selecting a desired amount of permitted motion. For instance, a surgeon's choice in implanting a pedicle screw system is generally limited to the cross-sectional size of the rod spanning between the pedicle screw assemblies, and larger rods require a larger yoke provided on the pedicle screw for receiving the rod therein. Even using systems that are designed to permit some degree of motion, such systems do not provide a surgeon the ability to optimize the motion permitted based on a particular patient, they do not allow a surgeon to adjust the mechanical behavior of the system through a linear range, and they do not allow a surgeon to adjust the mechanical behavior without full-scale revision surgery.

It would therefore be advantageous to provide a fixation device that significantly reduces, if not eliminates, the shortcoming, problems and risks noted above. As also understood from the foregoing, there is a long-felt need for improved spinal stabilization systems. Other advantages over the prior art will become known upon review of the Summary and Detailed Description and the appended claims.

BRIEF SUMMARY OF THE INVENTION

According to various embodiments presented herein, the present disclosure describes a fixation device, such as a screw, comprising one or more fenestrations which permit introduction of at least one other material or substance to through the fenestrations in the fixation device. In other embodiments, the fenestrations permit the fixation device to capture and retain material. In yet another aspect of the present disclosure, a method of using the fixation devices described herein is disclosed, including but not limited to in a surgical setting.

One particular aspect of the present disclosure involves a fixation device, such as an orthopedic pedicle screw or implant that is manufactured such that it includes one or more porous elements or fenestrations in order to aid in osteo-integration of the implanted fixation device. For instance, a pedicle screw (as one type of fixation device) may be additively manufactured using biocompatible materials such that the solid and porous aspects of the screw are fused together into a single solid construct with the porous elements interdigitated within and around various solid elements of the screw.

In yet another aspect, a surgical screw design having at least a portion or section incorporating a porous structure enables bony ingrowth through the porous section/portion of the screw, and thereby facilitates biocompatibility and improves mechanical characteristics. The porous elements of the screw may be designed to more closely resemble that of the patient's anatomy, in order to reduce discontinuities and stress risers at the bone/screw interface. Bony ingrowth within one or more porous elements of the screw in turn facilitates screw pullout strength, and may reduce the risk of loosening of a fixation device under dynamic loading situations.

In accordance with another aspect, an orthopedic device is disclosed to provide stabilization of the spinal column between anchorage locations on a minimum of two vertebral bodies comprising structural member(s) or spanning portions between each anchorage point, the device or system having the ability to provide stiffness, and the stiffness being variable in longitudinal and transverse planes relative to the spinal column or vertebral bodies.

The stiffness of the structural member(s) can be varied by adjustment of cross-sectional area properties. The stiffness of the structural member(s) can be varied by adjustment of helical coil spring tension/compression. The stiffness of the structural member(s) can be varied by adjustment of hydraulic pressure or volume. The stiffness of the structural member(s) can be varied by adjustment of pneumatic pressure. The stiffness of the structural member(s) can be varied by combining materials of differing properties.

An orthopedic device of the present invention may comprise at least two structural members, one of which has an outer cross-sectional profile that is smaller than the inner cross-sectional area of the other and is able to seat inside another structural member, the members being retained with a first end secured with a first vertebral body, and a second end operatively fixed with a second vertebral body. The orthopedic device may comprise at least two structural members, each of which has a non-uniform longitudinal cross-sectional area.

Structural members may have the ability to be retained at anchorage positions in any orientation along the transverse plane and, furthermore, have the ability to interface with one another in orientation along the transverse plane.

The orthopedic device may comprise at least two structural members whose geometry allows the two to be mated together and received into each anchorage point for securement at each level.

The orthopedic device may comprise a length appropriate helical coil spring with corresponding attachment fittings at each end. Each attachment fitting may have the ability to be secured to each attachment point. While securely attached to the helical coil spring, each fitting has the ability to translate radially (or rotationally) with respect to the anchorage point which effectively changes the geometric condition of the helical coil spring (reduce or enlarge the diameter). A length appropriate cylindrical rod may be located concentrically with the helical coil spring.

An orthopedic device which may comprise at least one helical coil spring (compression) concentrically located inside an additional helical coil spring (extension) the outer helical coil spring anchored to each vertebral body the inner helical coil spring retained to each anchorage point at each vertebral body. The anchorage points may interface with each helical coil spring having longitudinal adjustability, and additionally have the ability to receive a cylindrical rod concentrically to both helical coil springs for another opportunity to alter the stiffness of the device.

An orthopedic device may comprise a pressure vessel which is placed in the vicinity of and attached to each anchorage point, the pressure vessel having two or more independent, directional flow restricting valves. One valve may be for allowing fluid delivery into the pressure vessel, while another valve may serve to permit fluid exiting the pressure vessel. The valves may be disposed in a plurality of configurations including being integral with the structural members, being disposed on an external line thereto, or being disposed with a reservoir and system for adjusting the pressure/volume of the pressure vessel, any of such components (i.e., the valve, line, reservoir, and pressure system and actuator therefor) being disposed either subcutaneous or extracorporeal.

An orthopedic device may comprise a piston/cylinder configuration which is oriented longitudinally and secured to each anchorage point on each vertebral body, the piston having flow orifices of which the same could be adjusted to vary the volumetric flow rate and, ultimately, device stiffness.

An orthopedic device may comprise a pressure vessel which is located longitudinally between and attaches to each anchorage point, the pressure vessel additionally having an integrated reservoir which could be accessed post operatively for the purpose of introducing or removing working fluid to/from the pressure vessel.

An orthopedic device may comprise a pressure vessel which is located longitudinally between and attaches to each anchorage point, the pressure vessel having two independent, directional flow restricting valves. The first valve would allow a pressurized gas to be delivered inside the pressure vessel. The second valve would allow pressurized gas to exit the pressure vessel.

In an aspect of the invention, a spinal stabilization system securable with a plurality of vertebrae is disclosed including at least one anchor for at each of least two vertebrae, and a spanning structure extending between and securable with the anchors, wherein the spanning structure has an adjustable mechanical performance characteristic.

In some forms, the mechanical performance characteristic is a bending stiffness. The bending stiffness may be adjustable in orientation relative to the vertebrae. The bending stiffness may be adjustable in anterior, posterior, lateral, and torsional modes. The bending stiffness may be selected by selection of cross-sectional areas of the spanning structure. The bending stiffness may be selected by selection of differing materials for the spanning structure.

In some forms, the spanning structure may include an outer member and an inner portion, wherein the bending stiffness may be selected by selection of the inner portion. The inner portion may be provided after securing the outer member with the anchors. The inner portion may be comprised of a plurality of inner components, and the bending stiffness may be selected by selecting a number of the components to be disposed within the outer member. The bending stiffness may be adjusted by removal or addition of the inner components. The bending stiffness may be adjusted by orientation of the inner portion relative to the outer member. At least one of the outer member and the inner portion may have eccentrically positioned regions of reduced cross-sectional area, and rotation of the regions provides a direction for lowered stiffness.

In some forms, the mechanical performance characteristic is a compression/expansion stiffness. The spanning structure may include a spring including a plurality of coils. The stiffness may be adjustable by adjusting at least one physical characteristic of the spring. The physical characteristic may include at least one of the number of coils, the diameter of the coils, and the length of the spring. The coil spring may be an outer member, and the spanning structure may further include an inner portion, wherein the coil spring may provide a selectable and adjustable compression/expansion stiffness, and the inner portion may provide a bending stiffness.

In some forms, the spanning structure may includes a pair of springs each having a plurality of coils, wherein a first of the springs may provide a compression characteristic and a second of the springs may provide an expansion characteristic. The spanning structure may further include an inner portion, wherein one of the springs of the pair forms an outer spring, the other of the springs forms an inner spring, and the inner portion is disposed within the inner spring, the inner portion providing a bending stiffness.

In some forms, the spanning structure may include a piston assembly compressible and expandable along a longitudinal axis thereof. The piston assembly may be provided with compressible gas. The piston assembly may be provided with substantially incompressible fluid. The piston assembly may be provided with a damper. In some forms, the piston assembly is provided with fluid of mixed phases, a portion of the fluid being compressible gas and a portion of the fluid being incompressible liquid. In some forms, the piston assembly is provided with fluid, and the amount of fluid may be adjusted to adjust the mechanical performance characteristics. The system may further include a reservoir for fluid, wherein the piston assembly communicates with the reservoir, and the mechanical performance characteristics may be adjusted by increasing the fluid in the piston assembly by delivering fluid thereto from the reservoir and may be adjusted by decreasing the fluid in the piston assembly by delivering fluid therefrom to the reservoir. The piston assembly and reservoir may be connected via at least two one-way valves for fluid transfer there between. The reservoir may be a compressible bladder implanted subcutaneously.

In another aspect, a spinal stabilization system securable with a plurality of vertebrae is disclosed including at least one anchor for at each of least two vertebrae, and a plurality of spanning structures extending between and securable with the anchors, each spanning structure having an adjustable mechanical performance characteristic.

In some forms, each of the spanning structures is adjusted to impart a different stiffness characteristic between its respective anchors. In some forms, the mechanical performance characteristic of the spanning structures may be adjusted after being secured with the anchors. In some forms, the mechanical performance characteristic for at least one of the spanning structures is a bending stiffness, and the mechanical performance characteristic for at least one of the spanning structures is a compression/expansion stiffness.

In another aspect, a spinal stabilization system securable with a plurality of vertebrae is disclosed including at least one anchor for at each of least two vertebrae, and spanning structures extending between and securable with the anchors, the spanning structure having an adjustable mechanical performance characteristic, wherein the mechanical performance characteristic is adjustable after the spanning structure is secured with its respective anchors.

In some forms, at least one spanning structure mechanical performance characteristic is adjustable via a percutaneous incision in a patient's skin. In some forms, at least one spanning structure is adjustable via an end thereof. In some forms, the system may be adjusted via an implanted key or tool without an incision. In some forms, at least one spanning structure mechanical performance characteristic is adjustable via a hypodermic needle.

In some forms, at least one spanning structure includes a piston assembly, and the system further including a reservoir for fluid, wherein the piston assembly communicates with the reservoir, the mechanical performance characteristics of the piston assembly being adjustable by increasing the fluid in the piston assembly by delivering fluid thereto from the reservoir and adjustable by decreasing the fluid in the piston assembly by delivering fluid therefrom to the reservoir. The reservoir may be a compressible bladder implanted subcutaneously.

Incorporated by reference in their entireties are the following U.S. patents and patent applications directed generally to methods and apparatus related to surgical procedures, thus providing written description support for various aspects of the present disclosure. The U.S. patents and pending applications incorporated by reference are as follows: U.S. Pat. Nos. 7,957,824, 7,844,356, 7,658,610, 6,830,570, 6,368,325, 3,486,505 and U.S. Pat. Pub. Nos. 2010/0217336, 2009/0138020, 2009/0087276, 2008/0161817, 2008/0114370, and 2007/0270875.

Additionally, U.S. Pat. Nos. 8,758,357, 8,870,889, 9,198,678 and 9,642,633 are incorporated by reference for the express purpose of illustrating systems and methods for creating a device, such as the one described herein, using additive manufacturing or other techniques, wherein the device incorporates one or more patient-matched surfaces or is otherwise customized to a particular patient.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being approximations which may be modified in all instances as required for a particular application of the novel apparatus described herein.

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts and the equivalents thereof shall include all those described in the Summary, Brief Description of the Drawings, Detailed Description, Abstract, and Claims themselves.

The Summary is neither intended, nor should it be construed, as being representative of the full extent and scope of the present disclosure. Moreover, references made herein to "the present disclosure" or aspects thereof should be understood to mean certain embodiments of the present disclosure, and should not necessarily be construed as limiting all embodiments to a particular description. The present disclosure is set forth in various levels of detail in the Summary as well as in the attached drawings and the Detailed Description, and no limitation as to the scope of the present disclosure is intended by either the inclusion or non-inclusion of elements or components when describing certain embodiments herein. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below.

BRIEF DESCRIPTION OF THE DRAWINGS

The accompanying drawings, which are incorporated herein and constitute a part of the specification, illustrate embodiments of the disclosure, and together with the Summary and the Detailed Description serve to explain the principles of these embodiments. In certain instances, details that are not necessary for an understanding of the disclosure or that render other details difficult to perceive may have been omitted. It should be understood, of course, that the present disclosure is not necessarily limited to the particular embodiments illustrated herein. Additionally, it should be understood that the drawings are not necessarily to scale. In the drawings:

FIG. 5 shows a sectional view of a fixation device according to another embodiment of the present disclosure;

FIG. 6 shows an elevation view of a fixation device according to another embodiment of the present disclosure;

FIG. 7 shows a detailed view of the fixation device of FIG. 6;

FIG. 8 shows a sectional view of a fixation device according to another embodiment of the present disclosure; and FIG. 9 shows a perspective, sectional view of the fixation device of FIG. 8;

In the Figures.

Similar components and/or features may have the same reference number. Components of the same type may be distinguished by a letter following the reference number. If only the reference number is used, the description is applicable to any one of the similar components having the same reference number.

DETAILED DESCRIPTION OF THE INVENTION

The present disclosure has significant benefits across a broad spectrum of endeavors. It is the Applicant's intent that this specification and the claims appended hereto be accorded a breadth in keeping with the scope and spirit of the disclosure and various embodiments disclosed, despite what might appear to be limiting language imposed by specific examples disclosed in the specifications. To acquaint persons skilled in the pertinent arts most closely related to the present disclosure, preferred and/or exemplary embodiments are described in detail without attempting to describe all of the various forms and modifications in which the novel apparatus, devices, systems and methods might be embodied. As such, the embodiments described herein are illustrative, and as will become apparent to those skilled in the arts, may be modified in numerous ways within the spirit of the disclosure.

By way of providing additional background, context, and to further satisfy the written description requirements of 35 U.S.C. § 112, the following are incorporated by reference in their entireties for the express purpose of explaining and further describing the various tools and other apparatus commonly associated therewith surgical procedures, including minimally invasive surgery ("MIS") procedures: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

Referring now to FIGS. 1-9, varying embodiments of the present disclosure are shown. The fixation devices shown in FIGS. 1-9 preferably comprise a porous or fenestrated structure, which may be exposed at specific regions along the fixation device, and which aid with osteo-integration while increasing the mechanical stability of the device. Various benefits of the fixation device, which in a preferred embodiment is in the form of a screw, are described herein.

Figure 1:
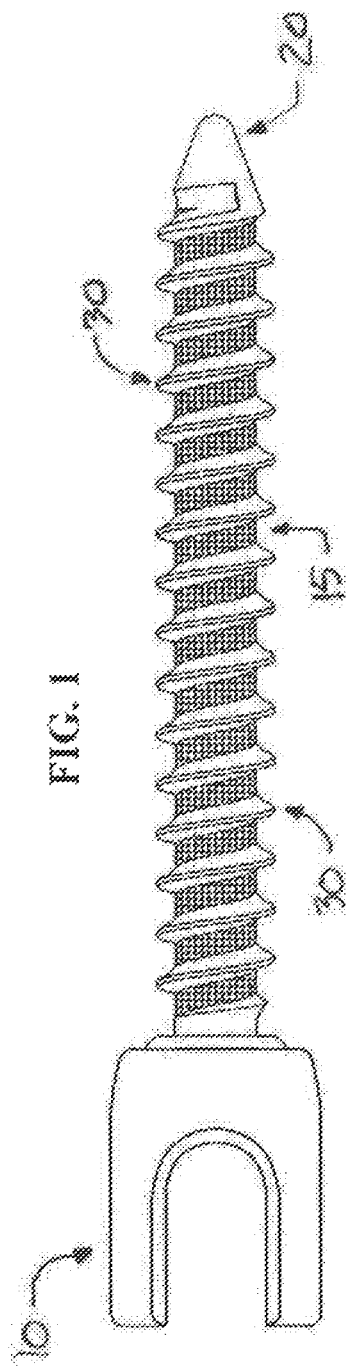
FIG. 1 shows a side elevation view of a fixation device according to one embodiment of the present disclosure.

In the embodiment of FIG. 1, the fixation device is provided in the form of a screw having a head portion 10 and a distal portion 20, with threads 30 located on the shaft 15 between the head portion 10 and the distal portion 20. In certain embodiments, the head portion 10 is affixed to the body of the fixation device, while in other embodiments the head is allowed to float and thereby provide a poly-axial screw assembly. In other embodiments, the head may be temporarily attached to the body of the fixation device. According to this particular embodiment, the porous or fenestrated structure is comprised of the shaft 15 of the screw, but not covering the head portion 10 or the threads 30. The number of fenestrations or porosity of the porous structure of the screw may be greater or lesser than depicted in FIG. 1.

Figure 2:
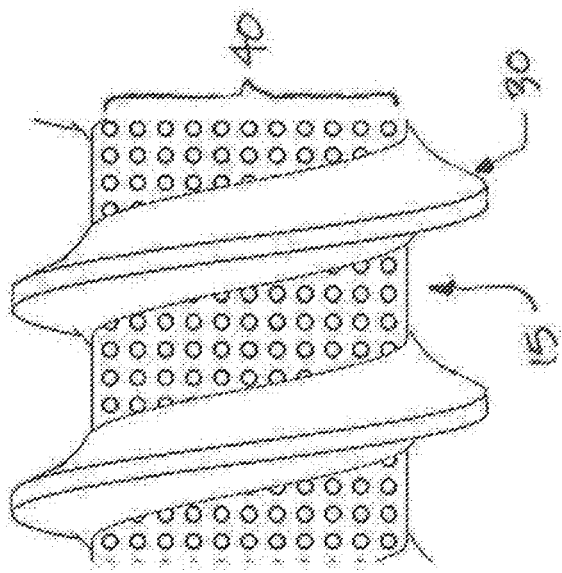
FIG. 2 shows a detailed view of the fixation device of FIG. 1.

Referring now to FIG. 2, a detailed view of the porous screw is depicted. In this drawing, the fenestrations 40 are arranged in series and extend substantially the entire width of the shaft 15 between the threads 30. In alternate embodiments, the fenestrations may be fewer in number than shown, and may not be uniform in their location and arrangement. The fenestrations may be circular or any other shape suitable for the fixation device. In alternate embodiments, the fenestrations extend even through the threads 30 of the screw.

The screw may be additively manufactured such that the porous structure may be exposed to the interfacing bone but also contained within the core of the screw. The screw may be additively manufactured, by way of example but not limitation, out of biocompatible alloys, including by using electron-beam melting or selective laser sintering methods to produce various surface finishes on the porous and solid aspects of the screw. The screw may be a manufactured as a single part, fixed angle screw, or may be poly-axial.

Figure 3:
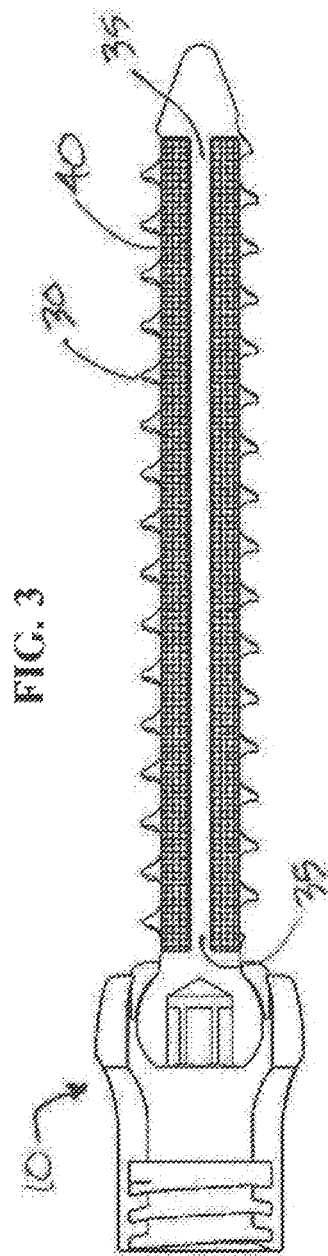
FIG. 3 shows a sectional view of a fixation device according to another embodiment of the present disclosure.
Figure 4:
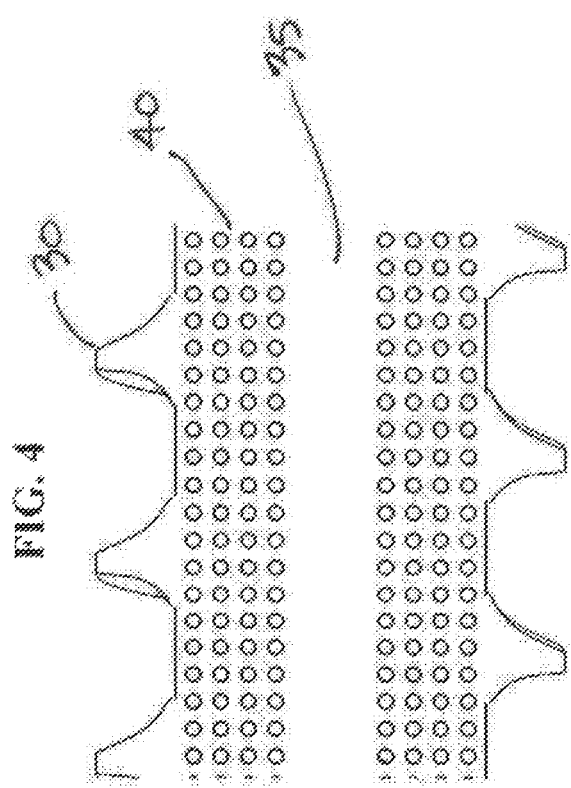
FIG. 4 shows a detailed view of the fixation device of FIG. 3.
Figure 10:
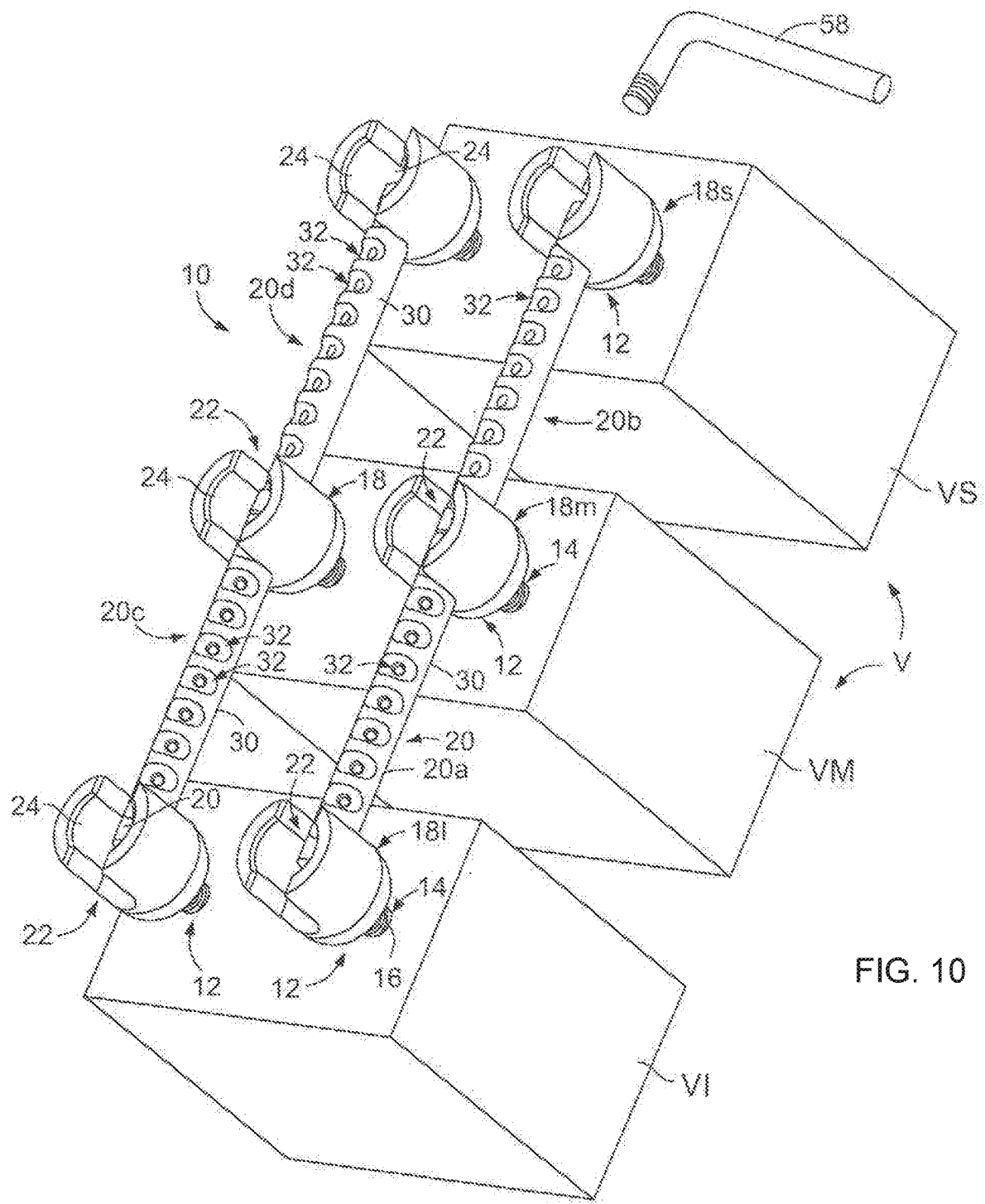
FIG. 10 is a perspective view of a first form of a spinal stabilization system secured with a plurality of representative adjacent vertebrae, the stabilization including a plurality of anchors in the form of pedicle screws and a plurality of spanning structures connecting the anchors, the spanning structures having a selectable and adjustable stiffness in bending or flexure provided by portions of reduced cross-sectional area.

Referring now to FIGS. 3-4, the screw may comprise a substantially hollow section that is in communication with the plurality of fenestrations 40. For example, as shown in FIG. 3, the screw may comprise a porous structure in a solid core to provide superior mechanical characteristics. The porous structure may be confined to only a certain region of the screw, or may extend substantially the entire length of the screw.

Referring now to FIG. 5, the fenestrations 40 may extend the entire width of the screw for substantially the entire length of the shaft 15, as shown. In this manner, the number of fenestrations 40 may be increased, thereby increasing the number of locations along the outer surface of the screw that either material can be introduced (via the screw) or material may be collected (via suction as described above). In embodiments, the screw may have a longitudinal channel 35 that runs lengthwise through the screw and permits material to be introduced through the longitudinal channel and into the plurality of fenestrations 40. For example, the longitudinal channel may be accessible from the head portion 10 of the screw, such that an operator may inject fluid or solid material into the longitudinal channel 35 and ultimately through the porous structure of the screw via fenestrations 40. In a similar manner, the fenestrations 40 (which surround the outer surface of the shaft 15 of the screw) may be used with vacuum or suction applied to the head portion 10 of the screw to retract material adjacent to the fenestrations 40 and either retained by the porous structure of the screw or within the longitudinal channel 35. By way of example, the screw could either be infused with bone morphogenetic protein or equivalent to enhance fusion between the screw and the patient's anatomy, or the screw could suction and retain autogenous blood into the fenestrations, which in turn stimulates boney ingrowth in the porous section of the screw. Variations on this embodiment are considered within the scope of the present disclosure.

Referring to FIG. 6, one embodiment comprises a varying array of fenestrations 40, which may increase or decrease along the length of the screw. As shown in FIG. 6, the number of fenestrations 40 may vary in a second portion of the screw, such that there is a decreased number or pattern of fenestrations 40' than at a different portion of the screw. In other portions of the screw, the shaft 15 may not comprise any fenestrations at all. This variation is best shown in the detailed view of FIG. 7. In this manner, material may either be collected or introduced via the screw only at desired locations along the length of the screw, which may be desirable given the particular bone density and surrounding anatomical features of a particular patient. In reference to FIGS. 6 and 7, in certain embodiments the longitudinal channel may comprise additional fenestrations in certain portions to better accommodate a particular patient's anatomy. For instance, a first portion of the longitudinal channel 35 is as depicted in FIG. 3, while a second portion of the longitudinal channel 35' may comprise a greater number of fenestrations and therefore a greater porosity.

Further variations of the embodiments described above are shown in FIGS. 8-9. For example, the fixation device may be a pedicle screw, which may be additively manufactured such that the solid and porous aspects of the screw are fused together into a single solid construct. In other embodiments, the solid and porous structure may be co-extensive with the porous elements interdigitated within and around various solid elements of the screw. Variations on these embodiments are considered within the spirit of the presently claimed invention.

The porous elements of the fixation device, screw or implant may be designed to more closely resemble that of a specific patient's anatomy. Accordingly, one advantage of the present disclosure is to promote bony ingrowth throughout the porous portions or sections of the implant, which in turn reduces the risk of loosening of the device under dynamic loading situations.

In still other embodiments, only a portion of the screw is manufactured with a porous surface. For example, the exposed porous aspects of the screw may be localized along the minor diameter of the thread form. The screw may therefore comprise hollow, porous or solid core elements to allow for varying levels of implant stiffness. These areas may be surrounded by a mostly solid thread form to facilitate smooth implantation and firm seating of the screw. Particular reference is made to FIGS. 3-4 when referring to this embodiment.

As referred to above, the porous elements of the screw may be designed with localized fenestrations, which may be at least partially accessible from the screw head, and thereby facilitate delivery of osteogenic agents such as bone-morphogenetic proteins, HA and or allograph or autograph tissue into the porous portions of the screw. This in turn allows for bony ingrowth and greater pullout resistance, as described above. The exposed porous structure may be located on the proximal portion of the screw, adjacent the screw head, in order to localize ingrowth. Localization of ingrowth may increase mechanical characteristics of the bone screw interface, and subsequently allow for easier implant removal in the case of revision surgery. The localized porous elements may be tapered outward to increase the interference fit of the porous elements with the surrounding anatomy.

The porous features are representative of porous cancellous bone with porosity preferably ranging between 30-80% to allow for ingrowth of osteocytes and supporting vasculature. Stated another way, the porous features, when compared to the solid features of the device, make up about 30-80% of the volume of the device. In a most preferred embodiment, the porosity is about 50%. In certain embodiments, the porous structure may be regular and geometric or irregular in form. In yet other embodiments, the porous density may be homogenous throughout the screw, or may be heterogeneous in order to attain desired stiffness and or improve the structural interface of the solid and porous elements.

The implant length and diameter may be pre-surgically planned to match the anatomical size of the patient's anatomy. The implant porosity and subsequent modulus may be pre-surgically planned to match the bone density of the intended patient. For example, in one embodiment, the surgical devices described above may be matched to an anatomic feature of a patient that has degenerated and needs to be restored. In another embodiment, the surgical device may be necessary to correct structural or physiological deformities present in the patient anatomy, and thereby serve to correct position or alignment of the patient anatomy. Other devices may be patient specific but do not serve a restorative or "structural" function.

The surgical devices described herein may be manufactured via additive manufacturing. In the context of spinal implants, the surgical devices may be used in all approaches (anterior, direct lateral, transforaminal, posterior, posterior lateral, direct lateral posterior, etc). Specific features of the surgical device can address certain surgical objectives, for example restoring lordosis, restoring disc height, restoring sagittal or coronal balance, etc. The fixation and surgical devices described herein may then be fabricated by any method. Fabrication methods may comprise the use of a rapid prototyping machine, a 3D printing machine, a stereolithography (STL) machine, selective laser sintering (SLS) machine, or a fused deposition modeling (FDM) machine, direct metal laser sintering (DMLS), electron beam melting (EBM) machine, or other additive manufacturing machine.

To add further stability to the seating and placement of the fixation devices described herein to the patient anatomy, the outer surfaces of the fixation device may further comprise one or more spikes or teeth or other surface features, which serve to contact and at least partially penetrate or "grip" the patient anatomy to secure the fixation device in place. In one embodiment, the surface features may be made of the same material and may be permanently attached to the fixation device. In another embodiment, the surface features may be comprised of an overlay, and/or may be made of a different material, such as the ones described herein, and may further be selectively inserted onto the fixation device(s) as desired.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the apparatus described herein, including, for example, width, length and thickness, and the size of the surgical apparatus.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials, rubber, latex, synthetic rubber, synthetic materials, polymers, and natural materials.

One having skill in the art will appreciate that embodiments of the present disclosure may be used in conjunction devices that employ automated or semi-automated manipulation. Various apparatus and implants described herein may be provided to facilitate or control the entry point, angular trajectory, height, and/or head orientation of a screw, for example. This is desirable, particularly with placement of screws in the human body, as it permits a surgeon/user to optimize spinal screw head alignment for subsequent rod insertion across multiple boney landmarks. Additionally, by controlling screw placement, a patient specific rod may be designed and manufactured to either match the pre-planned screw placement, or offer angular corrections in order to optimize curvature of the spine.

The present disclosure may also be advantageous in light of recent improvements in decentralized manufacturing. For example, surgical devices may soon be capable of fabrication in a number of different and convenient settings, including but not limited to an off-site manufacturing location, an on-site manufacturing location, using equipment present in a surgeon's clinic or offices or in a public or private hospital. For example, modules may be fabricated based on a particular patient need and immediately fabricated once the need is identified, and then provided directly to the surgeon.

In accordance with another aspect of the present disclosure, a plurality of forms and embodiments of spinal stabilization systems are depicted in FIGS. 10-31. In a variety of manners, these forms provide a user-surgeon with a range of choices for the motion that is permitted for spanning structures of the spinal stabilization system, the mechanical properties of the spanning structures including flexure, torsion, and/or compression and expansion, with linearly selectable mechanical properties, provide a surgeon with spanning structures that can provide a range of mechanical properties while being used with identical yokes of anchors, allow the surgeon to adjust the mechanical properties in situ, and allow the surgeon to adjust the mechanical properties post-operative without full-scale surgical revision.

Referring to FIGS. 10-14, a first form of a spinal stabilization system 10 of the present invention is illustrated secured with a plurality of representative vertebrae V. As illustrated, the vertebrae V include an inferior vertebra VI, a medial vertebra VM, and a superior vertebra VS. The stabilization system 10 includes a plurality of anchors 12 so that a pair of anchors 12 is provided for each vertebra V, as is well-known in the art. Each anchor 12 includes a screw 14 having a threaded shank 16 received in its respective vertebra V and includes a yoke 18. In some forms, the yoke 18 and shank 16 may be fixed relative to each other, such as by the anchor 12 being a unitary component or by being forming integral. In other forms, the anchor 12 may be a poly-axial anchor so that the yoke 18 may be oriented in a desirable manner once the anchor shank 16 is secured with the vertebra V.

The stabilization system 10 includes spanning structures 20 for connecting the vertebra V to control the relative movement there between. Each yoke 18 includes a channel 22 into which one or more spanning structures 20 is received for securement therewith. Once a spanning structure 20 is properly seated in the channel 22, a securement (not shown) generally referred to as a cap is driven atop the spanning structure 20 such as by being threaded into arcuate recesses 24 of the yoke 18 and to the sides of the channel 22.

Figure 11:
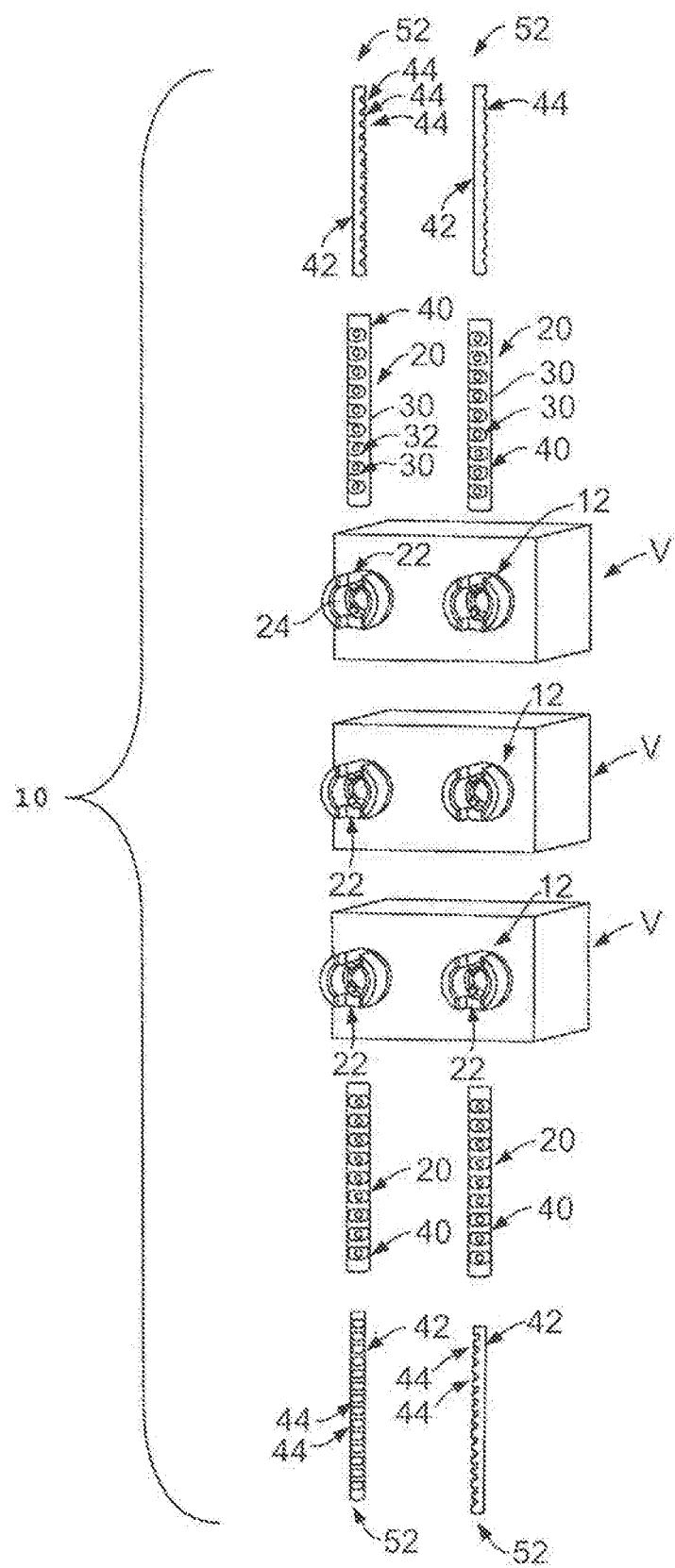
FIG. 11 is an exploded view of the stabilization system and vertebrae of FIG. 10 showing the spanning structures having an outer shell portion and an inner core portion, the shell and core each having portions of reduced cross-sectional area and being positionable relative to each other and to the anchors to provide a desired stiffness in a direction or region for the stabilization system.
Figure 12:
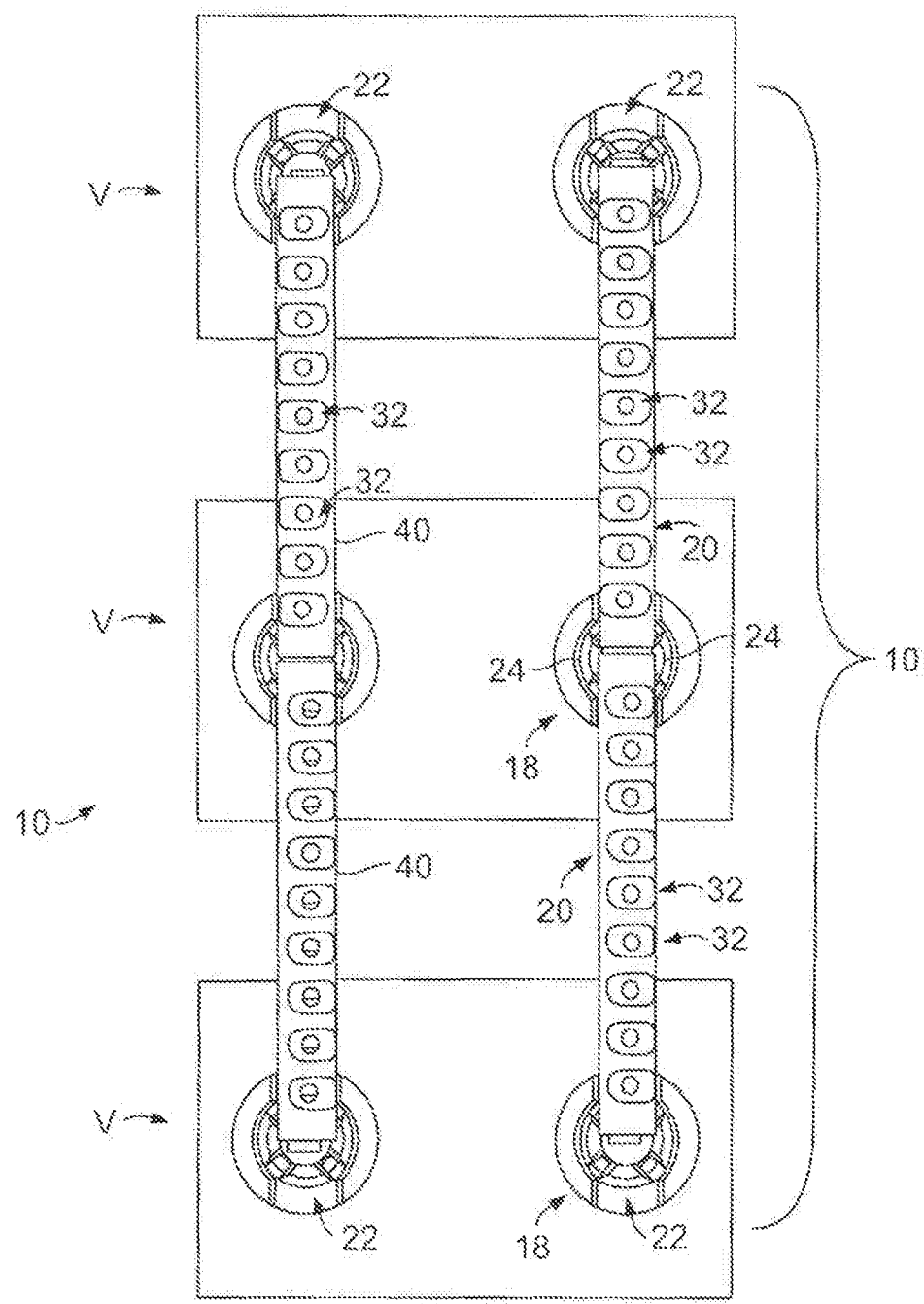
FIG. 12 is a top plan view of the stabilization system and vertebrae of FIG. 10 showing the spanning structures received within channels of yokes of the anchors.
Figure 13:
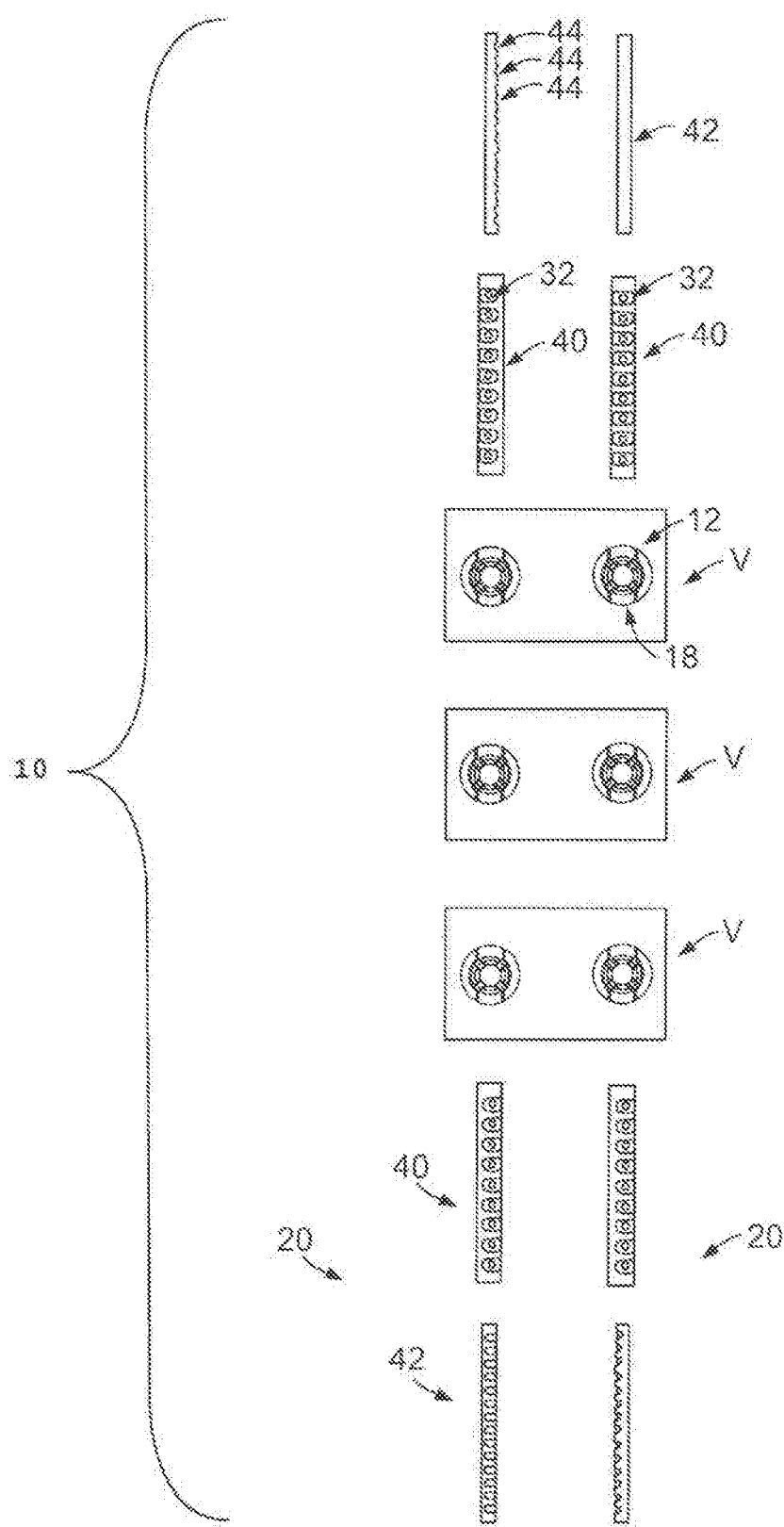
FIG. 13 is a exploded view of the stabilization system and vertebrae corresponding to FIG. 12 showing the reduced cross-sectional area portions of the cores having different orientations relative the shell reduced cross-sectional areas, as well as the anchors of the stabilization system, to provide different stiffness or mechanical performance characteristics to the different spanning structures.

As best seen in FIGS. 11 and 13, each spanning structure 20 is generally rod-like with an outer surface 30 with a plurality of cut-outs or scallops 32. The scallops 32 provide stress concentrators or, alternatively viewed, regions of lower stiffness for the spanning structure 20. When the spanning structure 20 is secured with the yokes 18, the scallops 32 are oriented in a direction in which it is desired to permit greater flexure between the anchors 12 to which the spanning structure 20 extends. To be clear, the scallops 32 are areas of reduced cross-sectional area that are eccentrically positioned relative to the central longitudinal axis of the spanning structure 20 so that orientation of the spanning structure 20 provides a distinct direction of lowered stiffness, and so that rotation of the spanning structure 20 alters the direction of lowered stiffness.

As can be seen, a first spanning structure 20a is secured between a first yoke 18I secured with the inferior vertebra VI and with a second yoke 18M secured with the medial vertebra VM while a second spanning structure 20b is secured between the second yoke 18M and a third yoke 18S secured with the superior vertebra VS. When secured, the scallops 32 of the first and second spanning structures 20a, 20b may have different radial orientations such that the flexure mechanical characteristics between the first and second yokes 18I and 18M are different than the flexure mechanical characteristics between the second and third yokes 18M and 18S.

It should also be recognized that the first spanning structure 20a cooperates with a third spanning structure 20c while the second spanning, structure 20b cooperates with a fourth spanning structure 20b to define the mechanical properties between their respective vertebrae V; thus, varying the orientations of scallops 32 for each of the four spanning structures 20a-20b serve to provide at least some of the mechanical properties for the stabilization system 10 as a whole. It should also be noted that the materials of the different spanning structures 20a-20b may be varied to provide or influence the mechanical properties of each.

In a further form of the spanning structure 20, the scallops 32 are formed on a shell member 40, and a core member 42 is received within the shell 40. In various forms, the core 42 may be of like or dissimilar materials to influence the mechanical properties to provide varying selected or selectable flexure properties, for instance.

In a preferred form, the core 42 also includes scallops 44 along its length, as best seen in FIGS. 11 and 13. When the core 42 is received within the shell 40, the core scallops 44 may be aligned (or misaligned) to varying degrees with the shell scallops 32. As should be evident, when the sets of scallops 44, 32 are aligned, such augments the flexure characteristics and, more appropriately, lessens the stiffness of the spanning structure 20 as a whole in a particular direction. When the scallops 44, 32 are largely misaligned, the decrease in stiffness provided by the different scallops 44, 32 is aligned in first and second directions. For the scallops 44, 32 merely being partially overlapping or relatively juxtaposed, the decrease in stiffness is distributed over the region between and including the scallops 44, 32. It should be noted that the scallops 32, 44 may be aligned or misaligned in both a radial direction (i.e., orientation in a 360 degree sweep) and in an axial direction.

The alignment of the scallops 32, 44 may be selected at any time prior to, during, or after implantation (securement in the yokes 18), as well as after the surgical procedure itself. To promote such adjustment, the core 42 may be provided with structure 50 on one or more ends 52 for engaging and rotating the core 42 relative to the shell 40.

Figure 14:
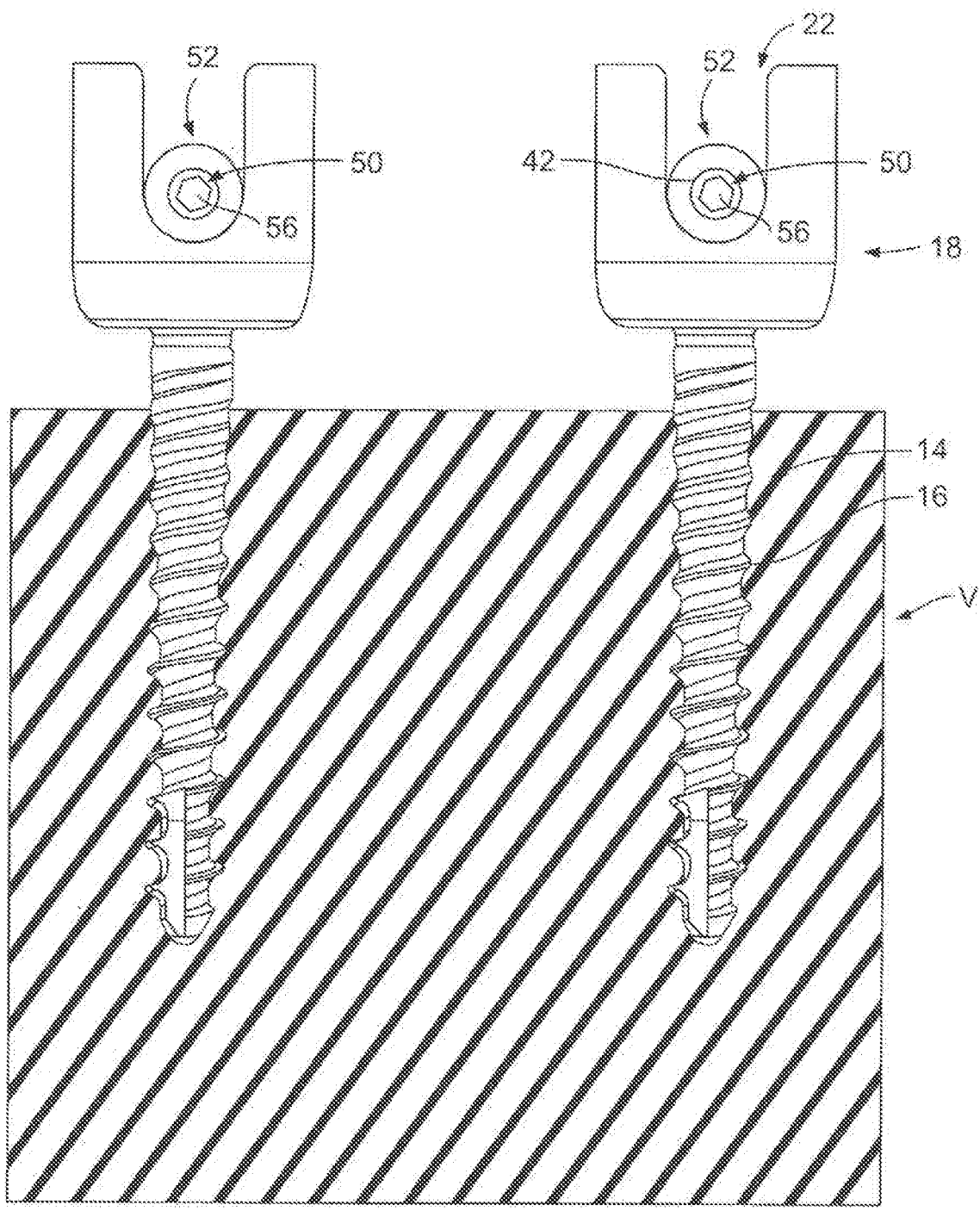
FIG. 14 is a side elevational view of a pair of anchors secured with a vertebra in cross-section, and of spanning structures of the stabilization system of FIG. 10 positioned for securement in the yoke channel thereof, an end of the spanning structure having structure for cooperating with a key or tool for adjusting the position of the core relative to the shell.
Figure 15:
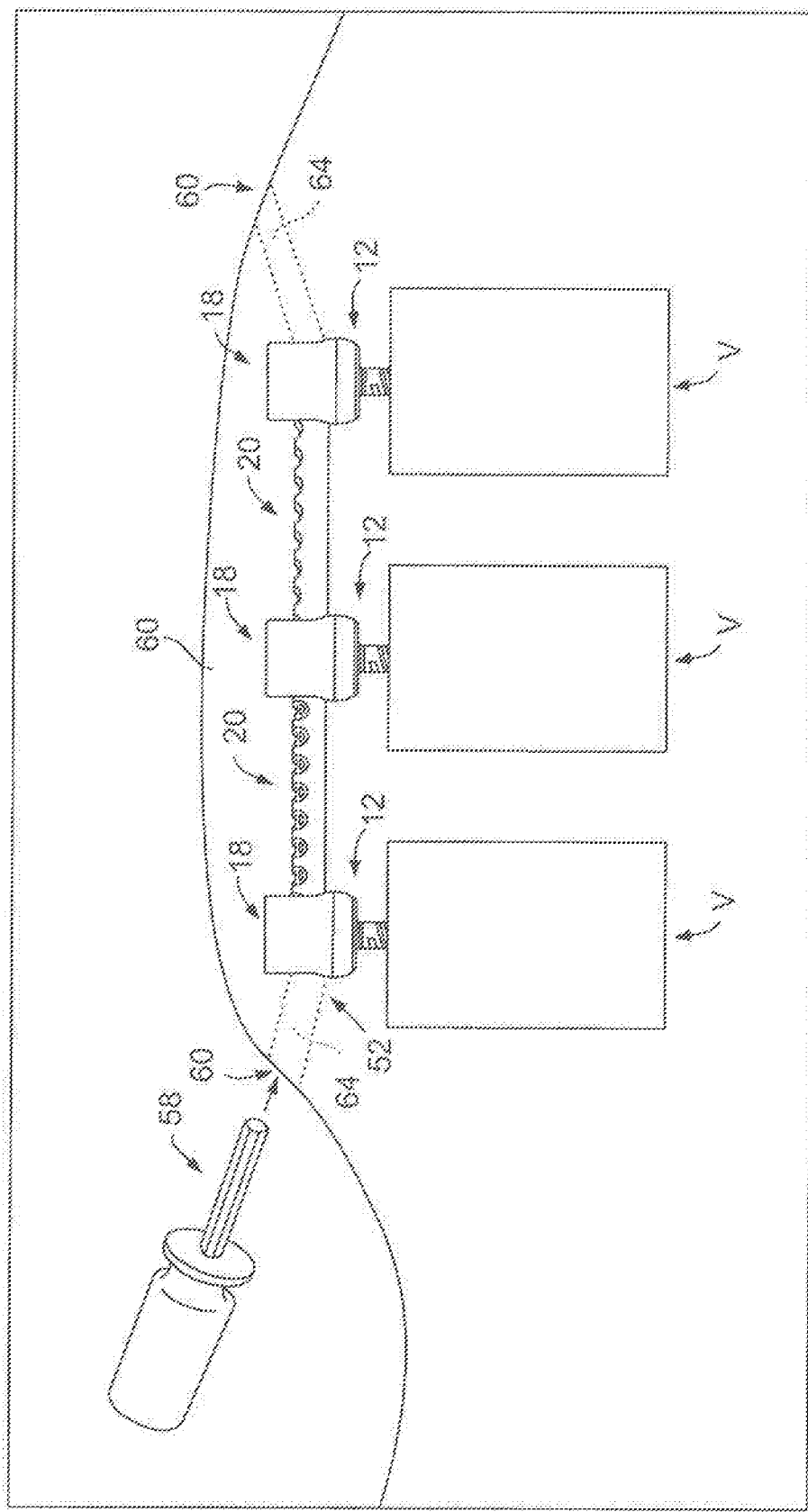
FIG. 15 is a representative side elevational view showing an implanted stabilization system having a layer of flesh covering the stabilization system, and access passages through the flesh provided by separate incisions, the access passages allowing access to end of spanning structures of the stabilization system.
Figure 16:
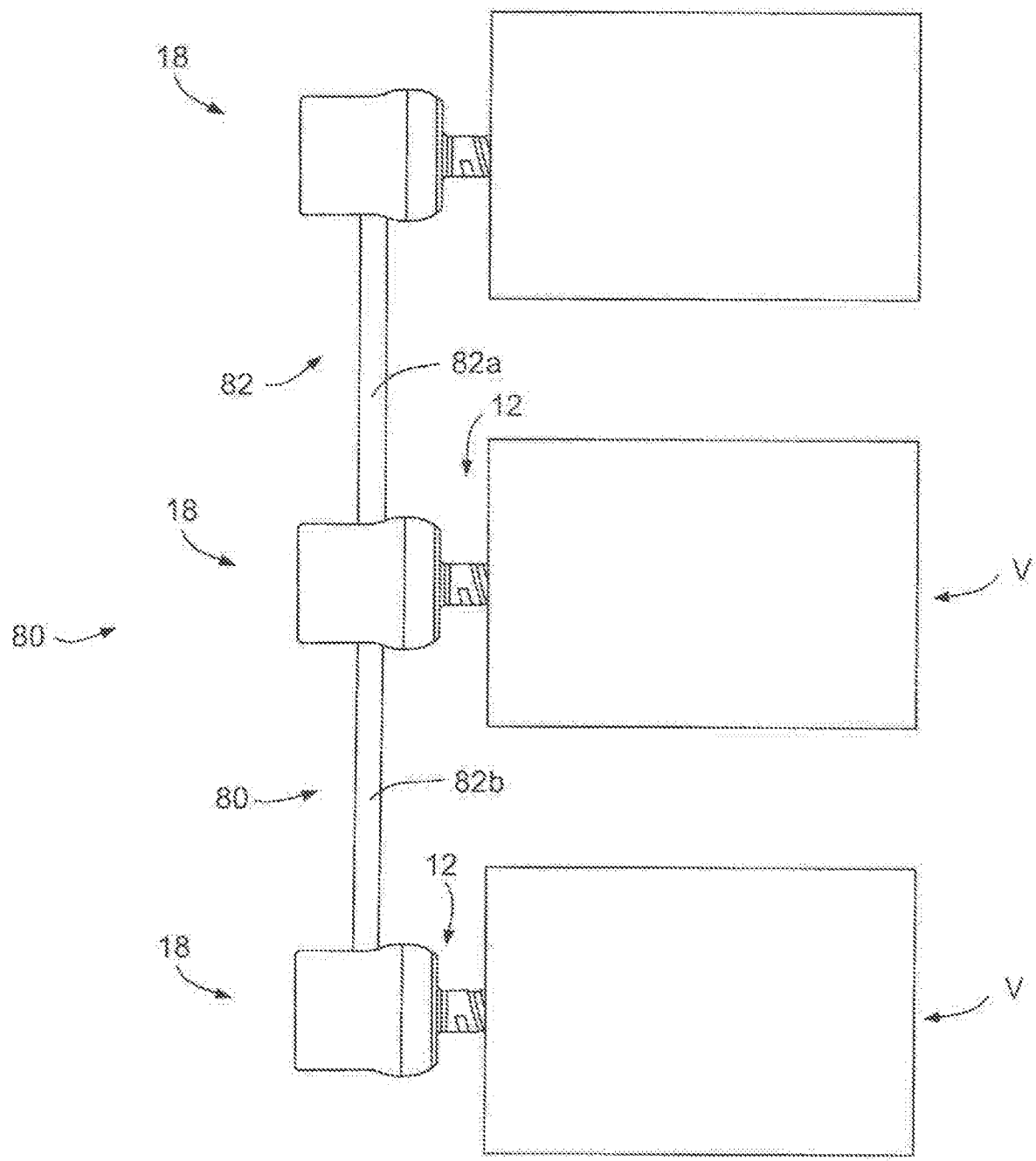
FIG. 16 is a representative view of a form of a stabilization system having spanning structures formed of different materials to provide different moduli of elasticity thereto.

As can be seen in FIG. 14, the core 42 includes a socket 56 shaped for receiving a key 58 (not shown). As an example, the socket 56 may be hexagonal (FIG. 14) for receiving a hexagonal key 58 (FIG. 15). In other forms, the key 58 may have a hook (not shown) or the like for axially advancing or withdrawing the core 42 along the axial direction of the shell 40. In another form, the socket 56 may include a section of internal threading for threadably receiving the key 58, the key 58 having slightly undersized threading (FIG. 10) for easy thread-receipt and effecting rotation in a single direction when fully advanced in the socket 56. Due to the threaded connection, such key 58 enables axial forces to be applied to the core 42 to advance/withdraw the core 42 within the shell 40.

The scallops 32, 44 may be cut at an oblique angle relative to a circumference of the shell 40 and/or core 42 so that the scallops 32, 44 may also facilitate or enable torsional distortion thereof. The depth, frequency, and/or size of the scallops 32,44 may be varied along the length of the shell 40 or core 42 so that the "spring equation" of the spanning structure 20 is non-linear, that is, so that the force required to achieve a certain amount of bending to the spanning structure 20 increases as the bending increases. Instead of the scallops 32, 44, either or both of the shell 40 and/or core 42 may simply be given a non-circular cross-section so that the bending characteristics are not the same throughout a 360 degree sweep.

Turning now to FIG. 15, the spinal stabilization system 101 is depicted as implanted with a layer 60 of a patient's flesh (including the surface skin) located atop the stabilization system 10. As can be seen, a small incision 62 may be made in the layer 60 to provide a passage or access 64 to the end 52 of a spanning structure 20. The key 58 may be inserted through the small incision 62 and the access 64 for connection with the spanning structure 20 socket 56. Accordingly, a major revision surgical procedure is not necessary to alter the mechanical performance characteristics (i.e., flexure or stiffness of the spanning structures 20), as such can be done with a minor procedure. It should also be noted that the core 42 may be entirely removed from the shell 40, which would also permit a new core 42 with greater or lesser stiffness to replace the previous core, all without having to remove the securements (i.e., caps) from the yokes 18.

As discussed above, the materials for the spanning structures 20 may be varied to provide different flexure or mechanical performance characteristics. Turning to FIG. 7, a form of a spinal stabilization system 80 is depicted similar to that of FIGS. 10-15, though simplified to illustrate spanning structures 82 and, in particular, to depict a first spanning structure 82a having a first modulus of elasticity and a second spanning structure 82b having a second modulus of elasticity that is different from the first, the modulus of elasticity determined by the material from which each spanning structure 82a, 82b is formed. As noted above, in the event a pair of spanning structures 82 is used in tandem to span between two vertebrae V, such as adjacent vertebrae V, the flexure characteristics are determined by a combination of the elastic moduli of the two spanning structures 82 of the pair.

It should be noted that reference to flexure characteristics and mechanical performance characteristics, as used herein, are meant to refer to how a spanning structure and/or a stabilization system performs under load, based on inherent materials properties and structural geometry. While in biomechanics, flexure and extension are generally thought of as being opposite, with respect to curving or bending of a spanning structure, these terms are one and the same. Additionally, these terms are intended in a broad manner to also include torsional distortion or twisting. Modulus of elasticity or elastic modulus is an inherent property of the material, regardless of shape or geometry. While stiffness and modulus of elasticity are typically thought of as linear descriptions of mechanical behavior dependent on shape and material, thereby equating them to a spring equation having a spring constant K (i.e., Force=K×Change in Length), it should be noted that these terms herein encompass a non-linear description of mechanical behavior such that force and distortion are not in direct proportion.

Figure 17:
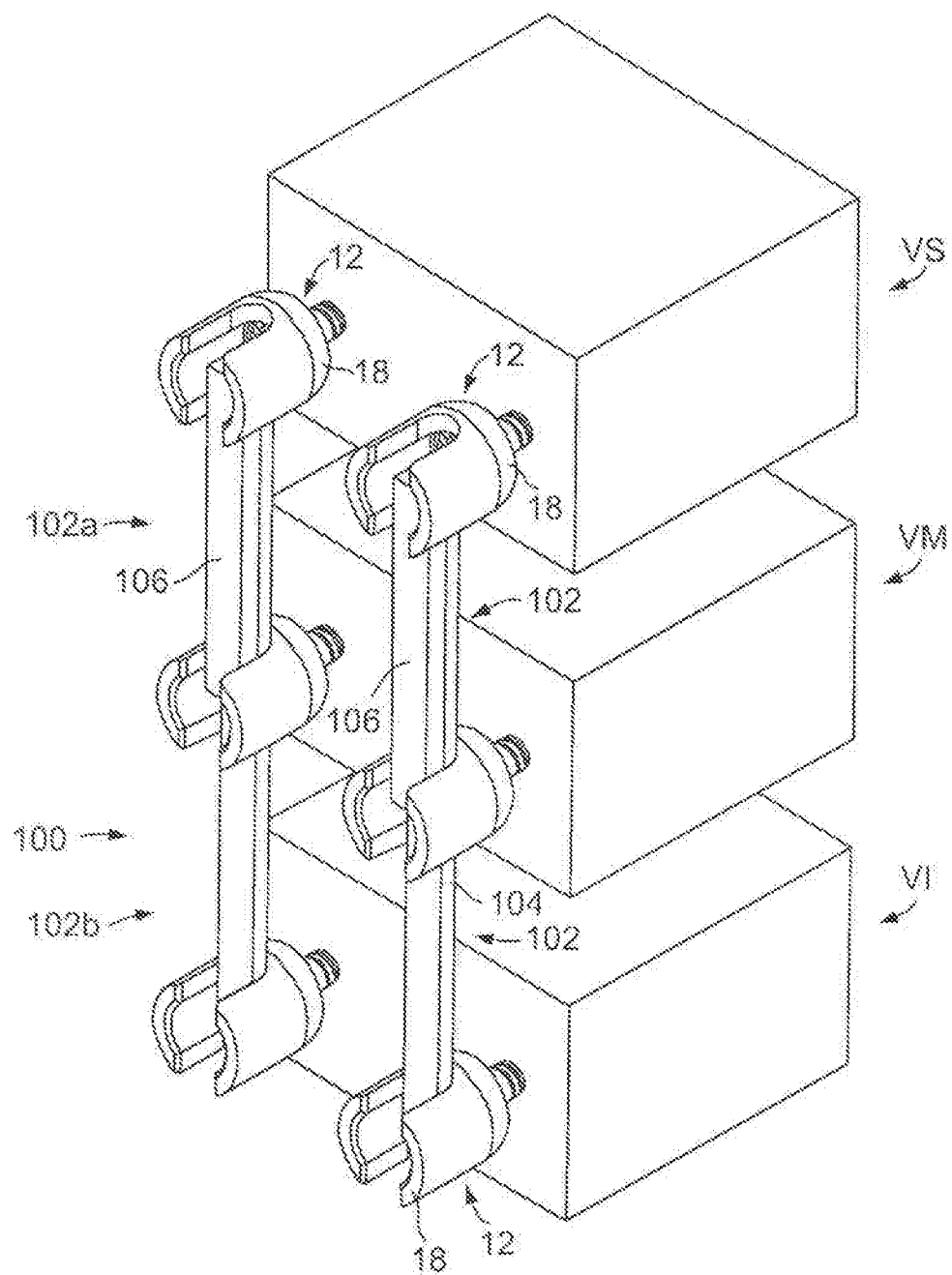
FIG. 17 is a perspective view of a form of a stabilization system secured with representative adjacent vertebrae, the stabilization system including spanning members that are provided as multiple pieces joined in the yoke of the anchor to provide different stiffness characteristics between different vertebral levels.
Figure 18:
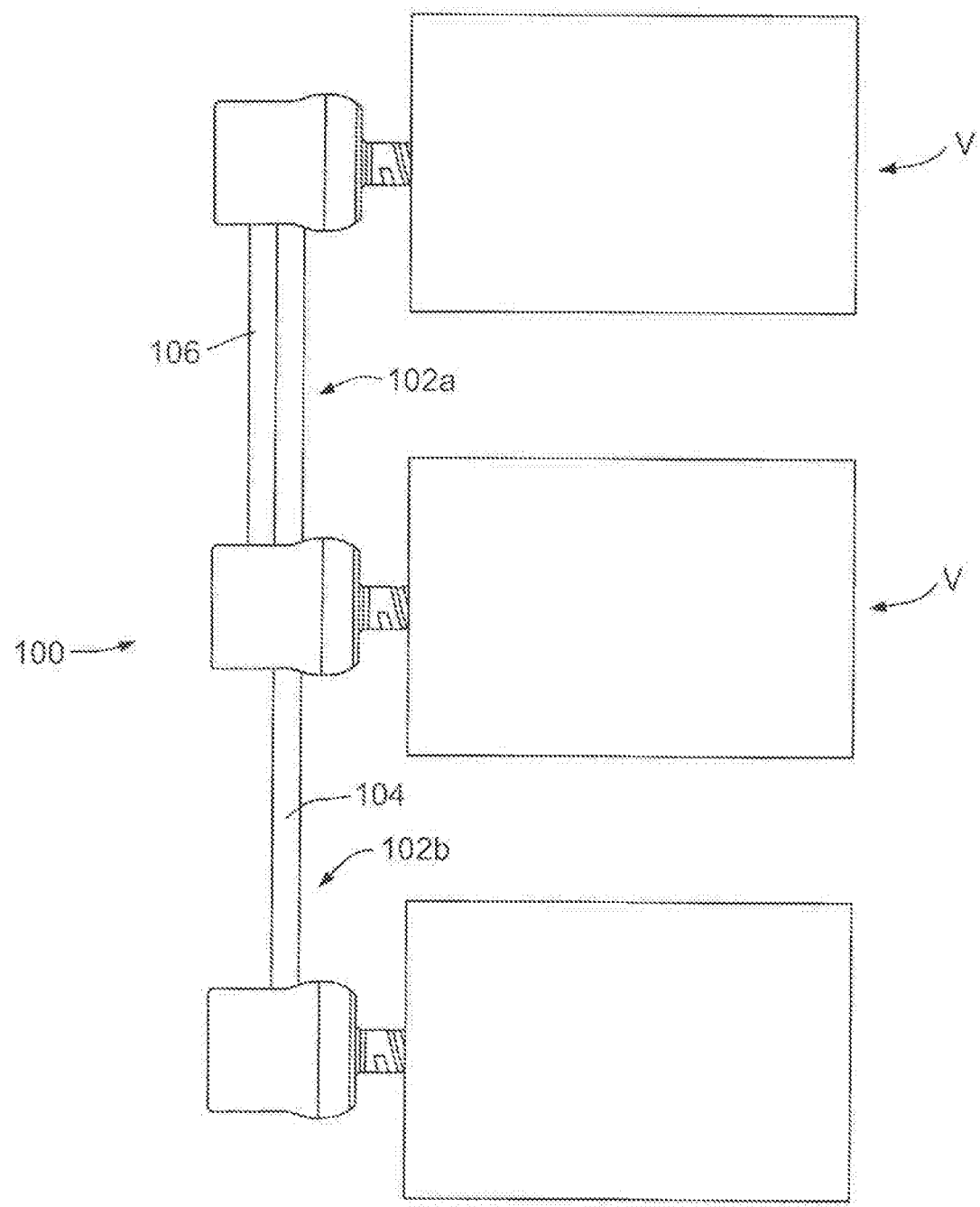
FIG. 18 is a side elevational view of the stabilization system of FIG. 17 showing spanning structures of an upper vertebral level having a greater cross-sectional thickness than spanning structures of a lower vertebral level.
Figure 19:
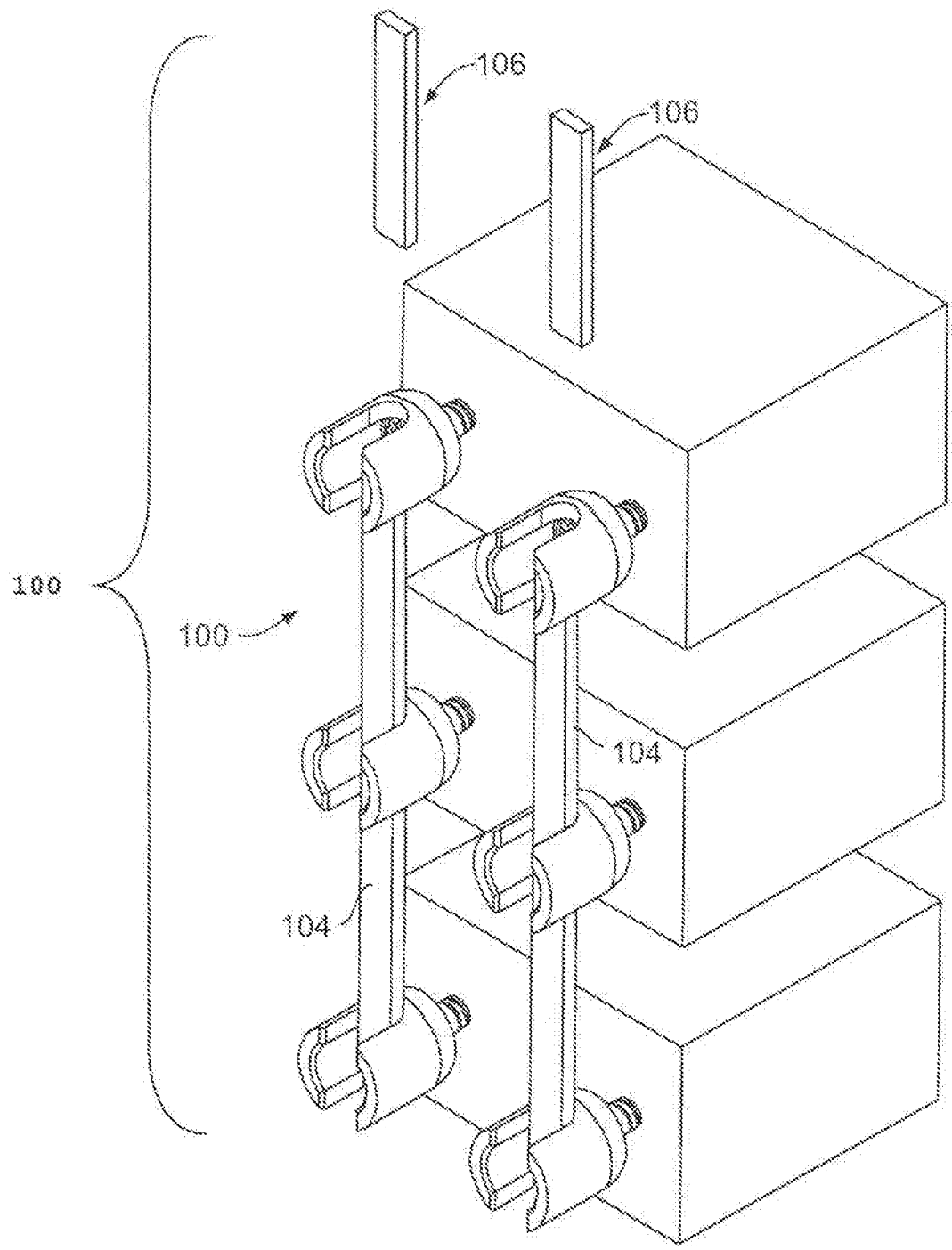
FIG. 19 is a partially exploded view of the stabilization system of FIG. 17 showing a portion of the spanning structure of the upper vertebral level removed, and showing unitary structures disposed in yokes for both the upper and lower vertebral levels.

Turning now to FIGS. 17-19, a further form of a spinal stabilization system 100 is illustrated having spanning structures 102 with different and selectable flexure characteristics. Again, the stabilization system 100 is largely similar to the stabilization systems 10 and 80, discussed above. However, the flexure characteristics of the stabilization system 100 of FIG. 17 are principally determined by the cross-sectional size of the spanning structures 102 as a whole between the vertebrae V.

More particularly, a spanning structure 102a between the superior and medial vertebrae VS and VM is approximately twice the cross-sectional size of the spanning structure 102b between the medial and inferior vertebrae VM and VI. As best seen in FIG. 19, the spanning structure 102a, 102b both include portions of a base spanning structure 104 that extends across and between each of the vertebrae V. However, the superior-medial spanning structure 102a additionally includes a secondary spanning structure 106, the combination of the same with the base spanning structure 104 defining the flexure characteristics therefor. Accordingly, the stiffness of the superior-medial spanning structure 102a is greater than the stiffness of the medial-inferior spanning structure 102b.

To the degree each of the spanning structures discussed herein does not exceed its elastic limit (or, more precisely, its change in shape does not exceed, for any portion thereof, a change beyond which deformation becomes permanent), such spanning structures may be modeled as a spring. However, each of the above-discussed forms of the spanning structures provides little, if any, expansion or compression along the longitudinal axial direction of the spanning structures.

Figure 20:
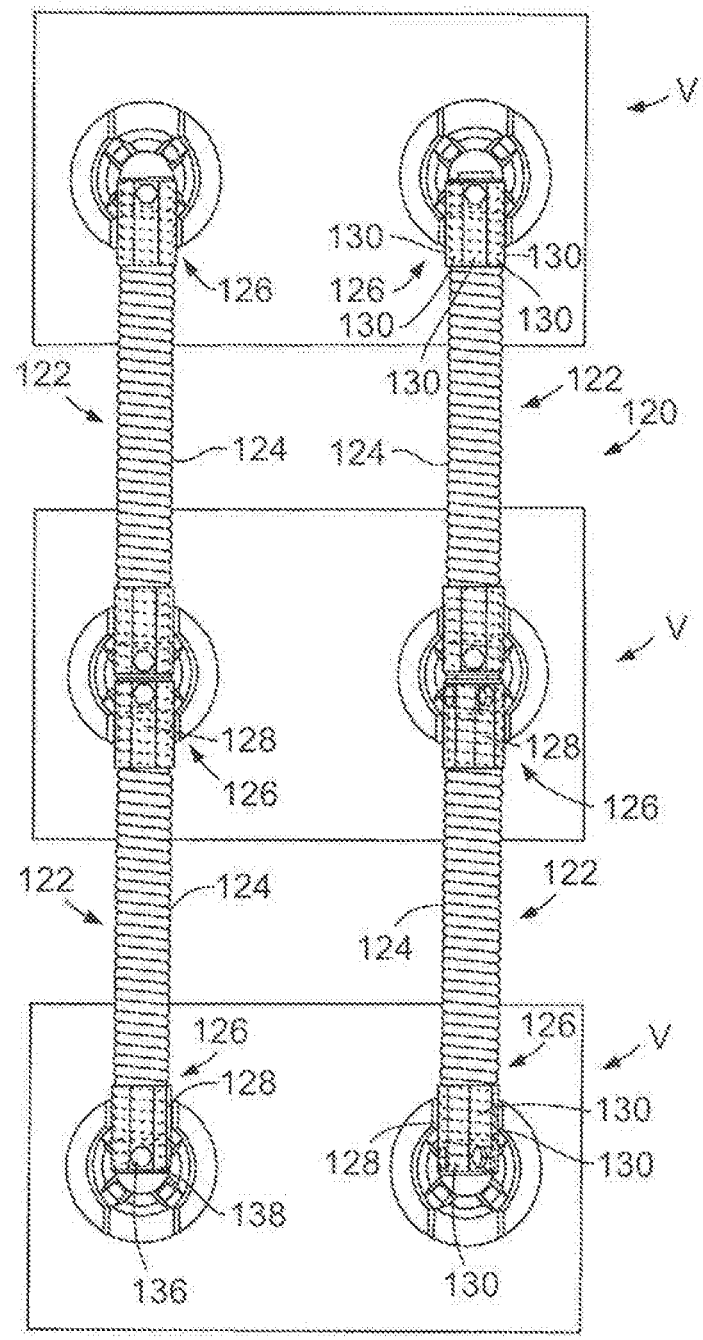
FIG. 20 is a top plan view of a form of a stabilization system secured with representative adjacent vertebrae, the stabilization system having spanning structures including spring coil portions securable with the channels of the yokes and having end fixtures that are graspable or manipulable with a tool for rotating the end fixtures to alter the stiffness characteristics of the spanning structures.
Figure 21:
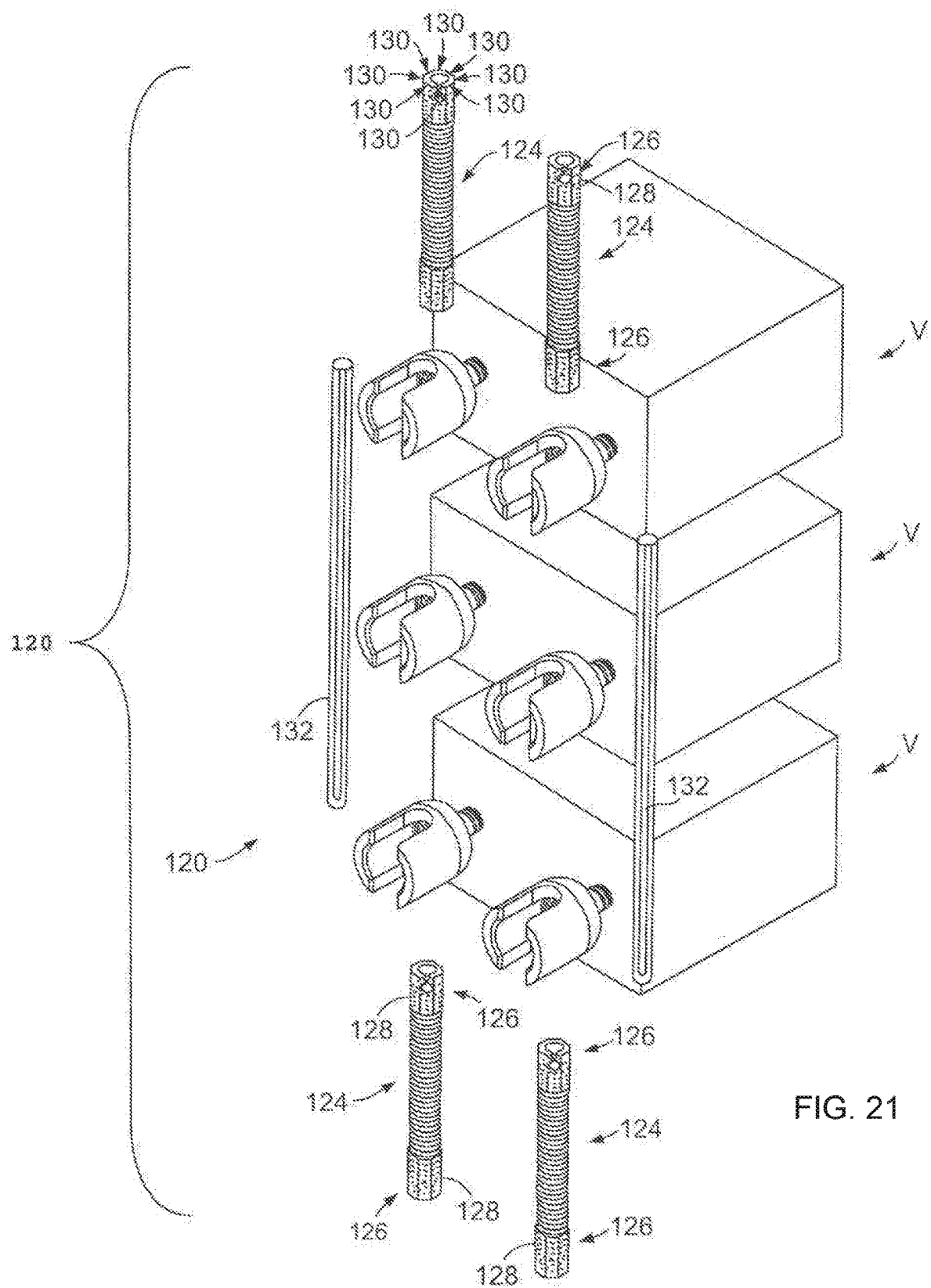
FIG. 21 is an exploded perspective view of a form of the stabilization system of FIG. 20 showing rod-like central core portions receivable within the coil portions of the spanning structure.

Turning now to FIGS. 20 and 21, a further form of a spinal stabilization system 120 is shown having spanning structures 122 that include a coil spring portion 124 that allows the stabilization system 120 to accommodate expansion and contraction of the spanning structure 122 along its longitudinal axis. The stabilization system 120 includes anchors 12 and yokes 18, like each of the above-described embodiments, the spanning structures 122 being received in the yokes 18 and secured therein by a securement such as a cap.

In order to secure the spanning structure 122 with the yokes 18, each end 126 thereof includes an end fixture 128. The end fixture 128 may have any shape, provided that the end fixture 128 is generally sufficiently rigid as to be compressed within the yoke 18 by the securement. The end fixtures 128 are illustrated as being generally octagonal so that flats 130 are formed on the end fixture 128, a pair of the flats 130 contacting the sides of the yoke channel 22, a flat 130 contacting the bottom interior of the yoke channel 22, and a flat 130 being outwardly facing for contact with the cap when secured in the yoke 18. As noted, other configurations of the end fixture 130 may be provided, such as a square or circle; however, the octagonal shape has the benefit of a leading flat 130 that is shorter than the width of the yoke channel 22 to assist in initial advancement of the end fixture 128 into the channel 22. The octagonal shape also provides the benefit of the flats 130 themselves for engaging with the yoke 18 and cap, which serves to provide good compressive contact and serves to retard rotation of the end fixture 128 within the yoke 18 after securement.

Each spanning structure 122 is provided with a single coil spring 124. For the various spanning structures 122 illustrated, each can be provided with varying mechanical performance characteristics. For instance, the effective (i.e., when implanted) spring constant for each coil spring 124 can be selected based on the length of the coil spring 124, a number of turns in the coil spring 124, a diametral size of the coil spring 124, and pre-stressing of the coil spring 124 when implanted.

A surgeon can easily adjust or alter the performance characteristics by altering the above aspects of the coil spring 124. As best seen in FIG. 20, each end fixture 128 is provided with at least one opening 136. A tool (not shown) can be inserted into the end fixture 128 through an end passage 138 and into the opening 136. The tool can then be used to rotate the end fixture 128 relative to the other end fixture 128, thus pres-stressing the coil spring 124 as well as changing the diametral size and number of coils in the spring 124. In one form, a first of the end fixtures 128 may be positioned in a yoke 18, while the other is manipulated as described. Alternatively or in addition, the first end fixture 128 may be secured in a yoke 18, and the other end fixture 128 may be pulled longitudinally, along the axis of the spanning structure 120, to remove it from the yoke 18; the end fixture 128 may then be rotated and returned within its yoke 18 when the desired number of turns has been made. In order to perform such, loosening of a cap or securement for the end fixture 128 that is rotated may be necessary, particularly if such procedure is performed in a post-operative procedure.

While the spanning structures 122 including the coil springs 124 provide expansion and compression along the longitudinal length, they provide less stiffness in the other directions. Accordingly, a core 132 may be inserted within the coil springs 124. The cores 132 may be provided with varying mechanical performance characteristics, as has been discussed herein, such as by being formed of materials with different elastic moduli.

As shown in FIG. 21, the core 132 may span a plurality of vertebrae V. Alternatively, the cores 132 may span only to two adjacent vertebrae V. In a preferred form, the cores 132 may be removable and replaceable without removal of the securement and end fixtures 128. In this manner, the cores 132 may be changed by the above-described simple incision procedure. Towards this end, the cores 132 may be provided with structure assisting in their removal, such as structure similar to the above-described socket 56 and key 58.

Figure 22:
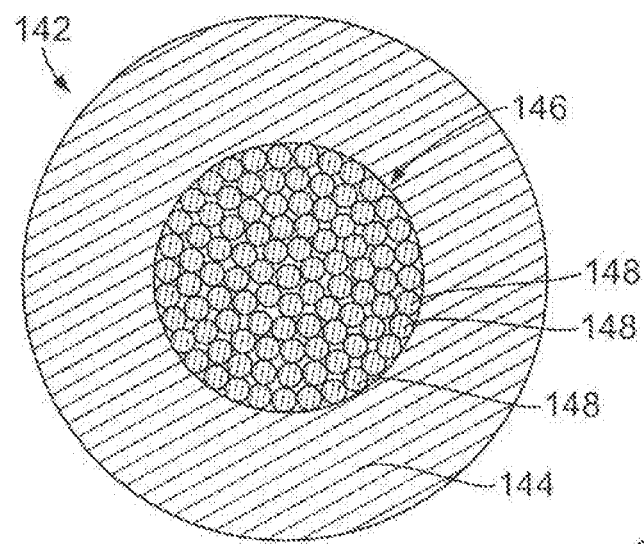
FIG. 22 is a side elevational view of a form of a spanning structure for use with anchors, the spanning structure having a outer sheath or casing which permits addition or removal of core strands there within for providing a selected stiffness to the spanning structure.
Figure 23:
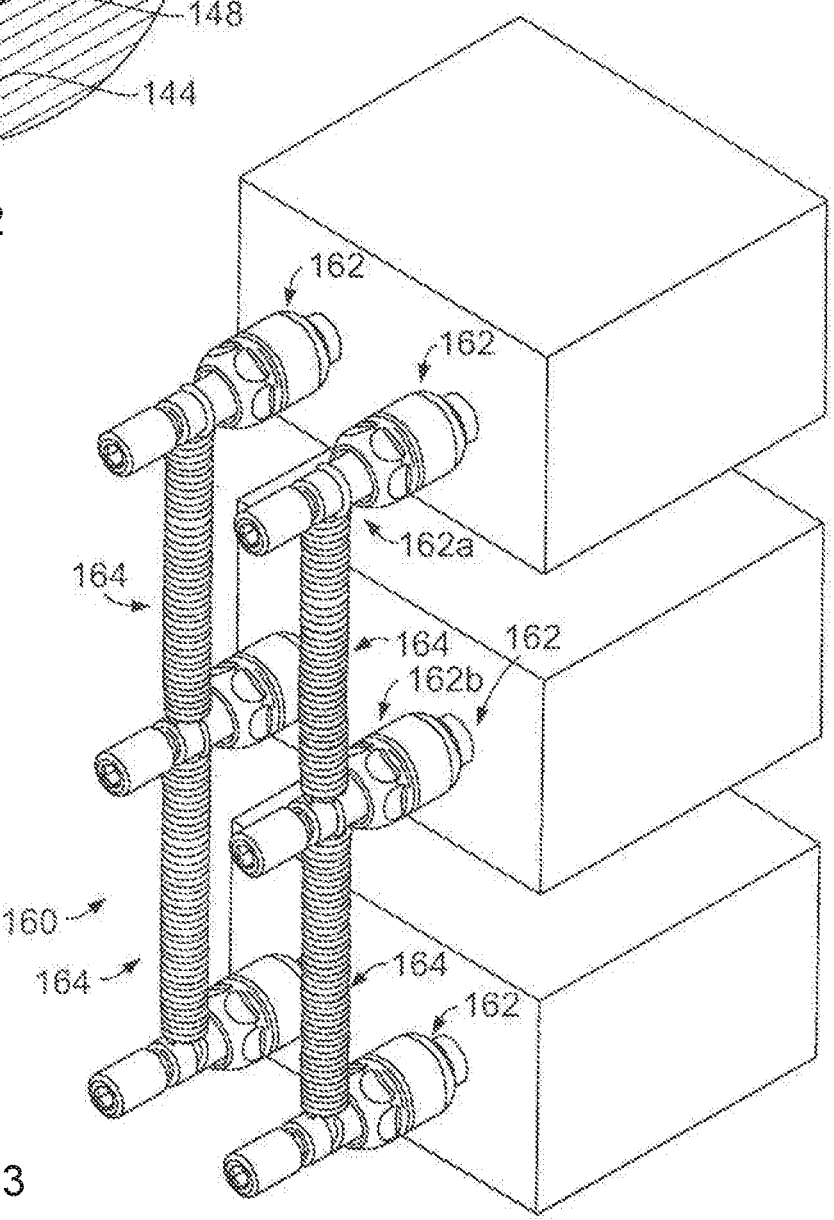
FIG. 23 is a perspective view of a form of a stabilization system secured with representative adjacent vertebrae, the stabilization system having anchors with posts for engaging with spanning structures having coil springs with end loops.
Figure 24:
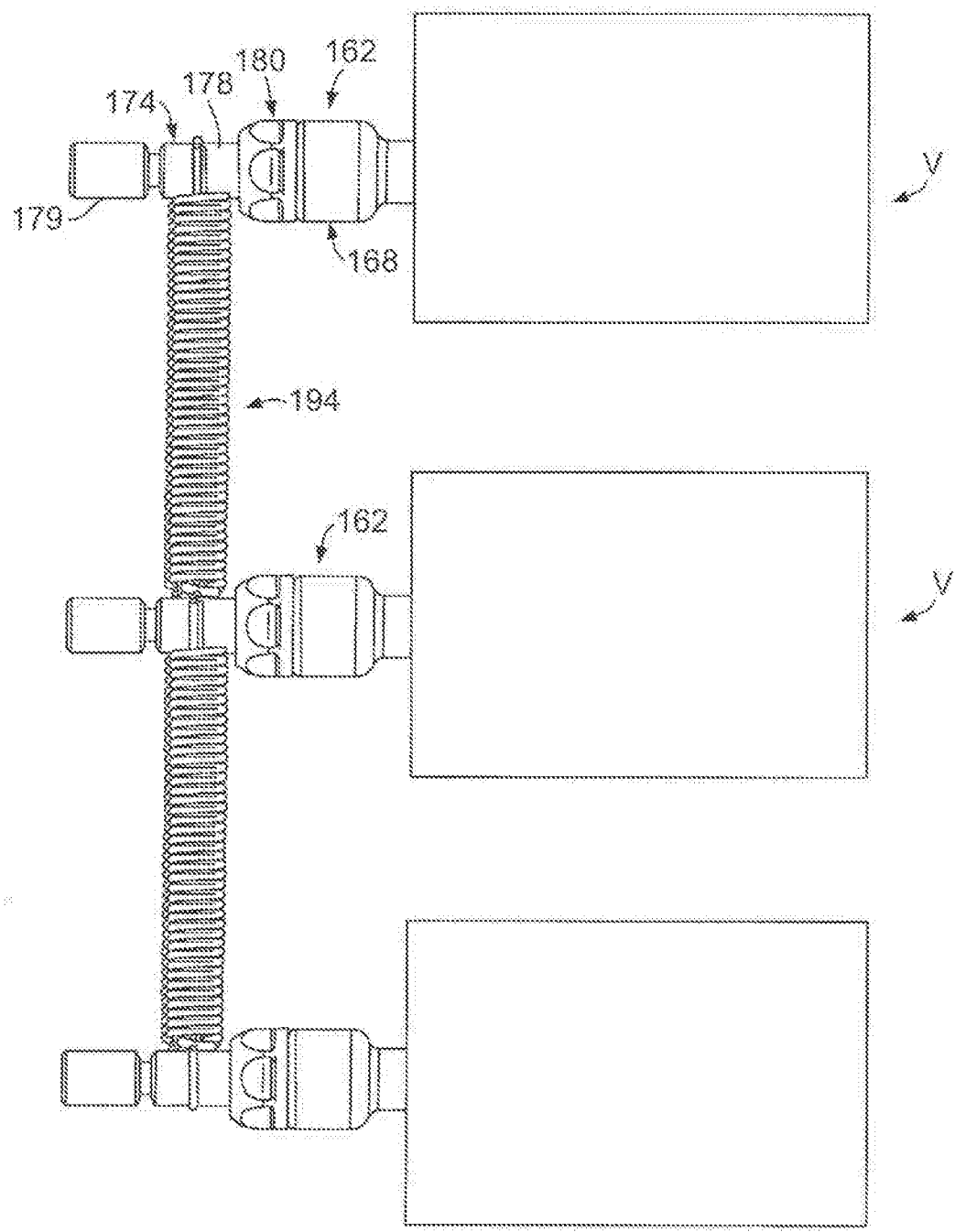
FIG. 24 is a side elevational view of the stabilization system of FIG. 23.
Figure 25:
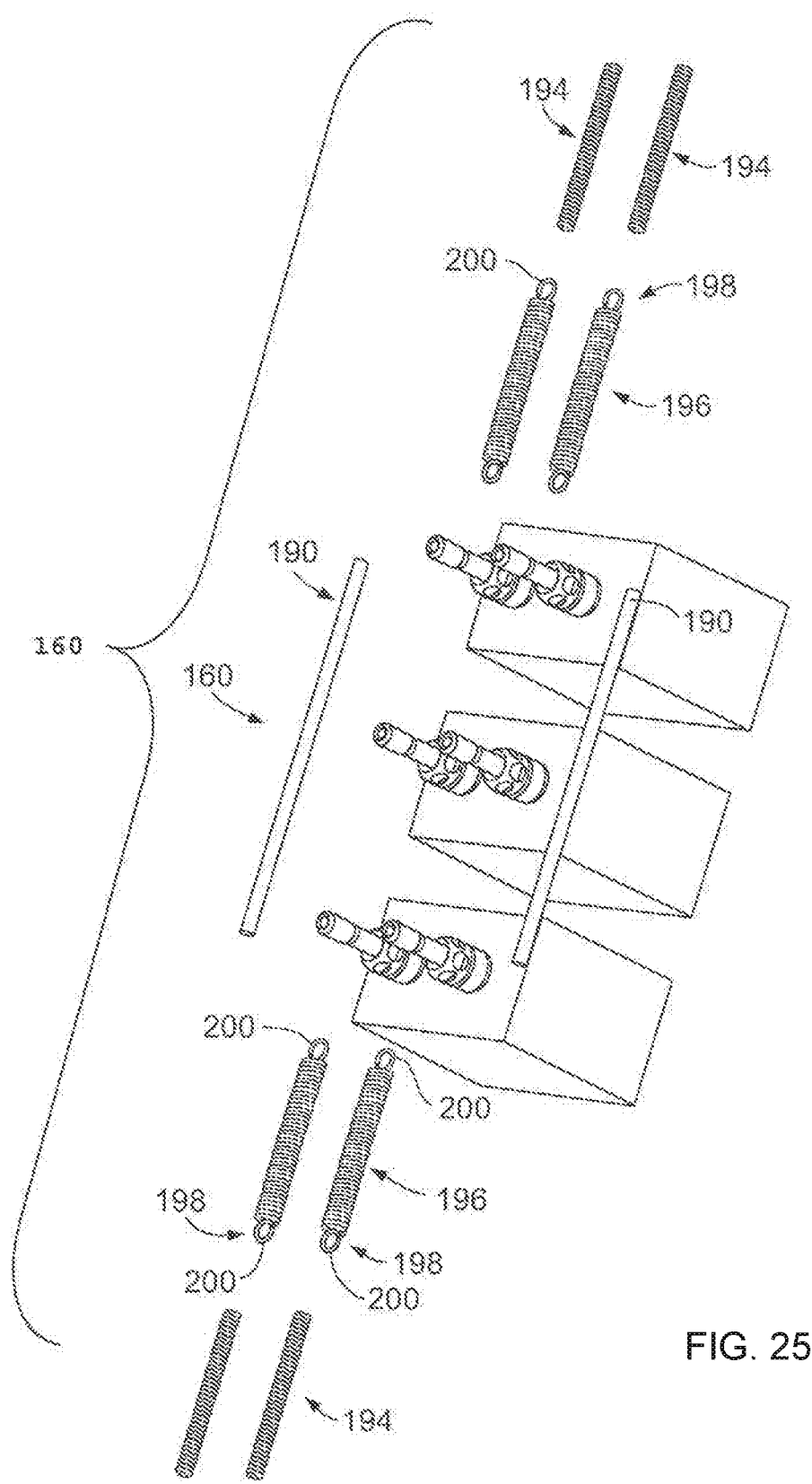
FIG. 25 is an exploded perspective view of a form of the stabilization system of FIG. 23 showing the coil springs as outer coil springs, showing inner coil springs, and showing central rod-like core members for providing desired stiffness characteristics to the spanning structures.

In a form similar to the spanning structures 20 or 122, a stabilization system may be provided with spanning structures 142 that are essentially tubular casings 144, having a hollow bore 146, and a plurality of strands 148 of material are received within the bore 146, as depicted in FIG. 22. The number and/or size of the strands 148 thus cooperate with the casing or sheath 144 to provide the flexure characteristics for the spanning structure 142. In general, the strands 148 would generally be rod or wire-like with a constant diameter and inserted within the casing 144 to provide a desired stiffness. However, the individual strands 148 may also have non-uniform cross-sections, for the reasons discussed herein, and/or may have non-uniform lengths. For the latter, the strands 148 could be staggered or otherwise positioned relative to each other so that the combination of the strands 148 and the casing 144, through any particular cross-section, determine the stiffness thereat.

The number or configuration of the strands 148 may be modified at any desired time, such as post-implantation or post-operatively. That is, it may be convenient to initially implant and secure the casing 144 with the yokes 18, and then insert the strands 148. Furthermore, later minor surgical procedures could be performed to provide additional strands 148, or to remove strands 148, based on the conditions experienced by the patient.

It is known that the bone-screw interface, such as for a pedicle screw, improves over time in the absence (or minimization) of loading on the interface. Therefore, it may be desirable for a portion of the stabilization systems to be implanted with minimal loading on the anchors 12, and a portion to be subsequently adjusted or added to increase the loading on the anchors 12 or the stiffness of the stabilization system.

For instance, the casing 144 may be implanted (or the above-described shell 40 or coil spring 124, for instance) with the bore 146 substantially empty. After a period of time; a minor surgical procedure including a small incision proximate the spanning structure, as is described for FIG. 15, may be performed to increase the stiffness such as by inserting strands 148 into the bore 146.

In a reverse manner, decreasing the stiffness of the spanning structures may be performed in accordance with that discussed for FIG. 15 by making the small incision and removing strands 148 from the bore 146.

In another form of spinal stabilization system 160, shown in FIGS. 23-26, anchors 162 are provided for securing spanning structures 164 having springs. The anchors 162 include a threaded shank 166 as described above and a head 168 which may or may not be polyaxially adjustable, as described. In contrast to the above forms, the head 168 does not form a yoke 18 having a channel 22, instead having a cylindrical recess 170 defined by an upstanding collar 172.

An anchor post 174 cooperates with the head 168 for securing the spanning structures 164 with the anchors 162. The post 174 includes a widened base 176 received in the recess 170 and an upstanding post portion 178. The head collar 172 is threaded (either internally or externally) for receiving a nut 180 thereon for securing the anchor post 174 with the head 168.

Figure 26:
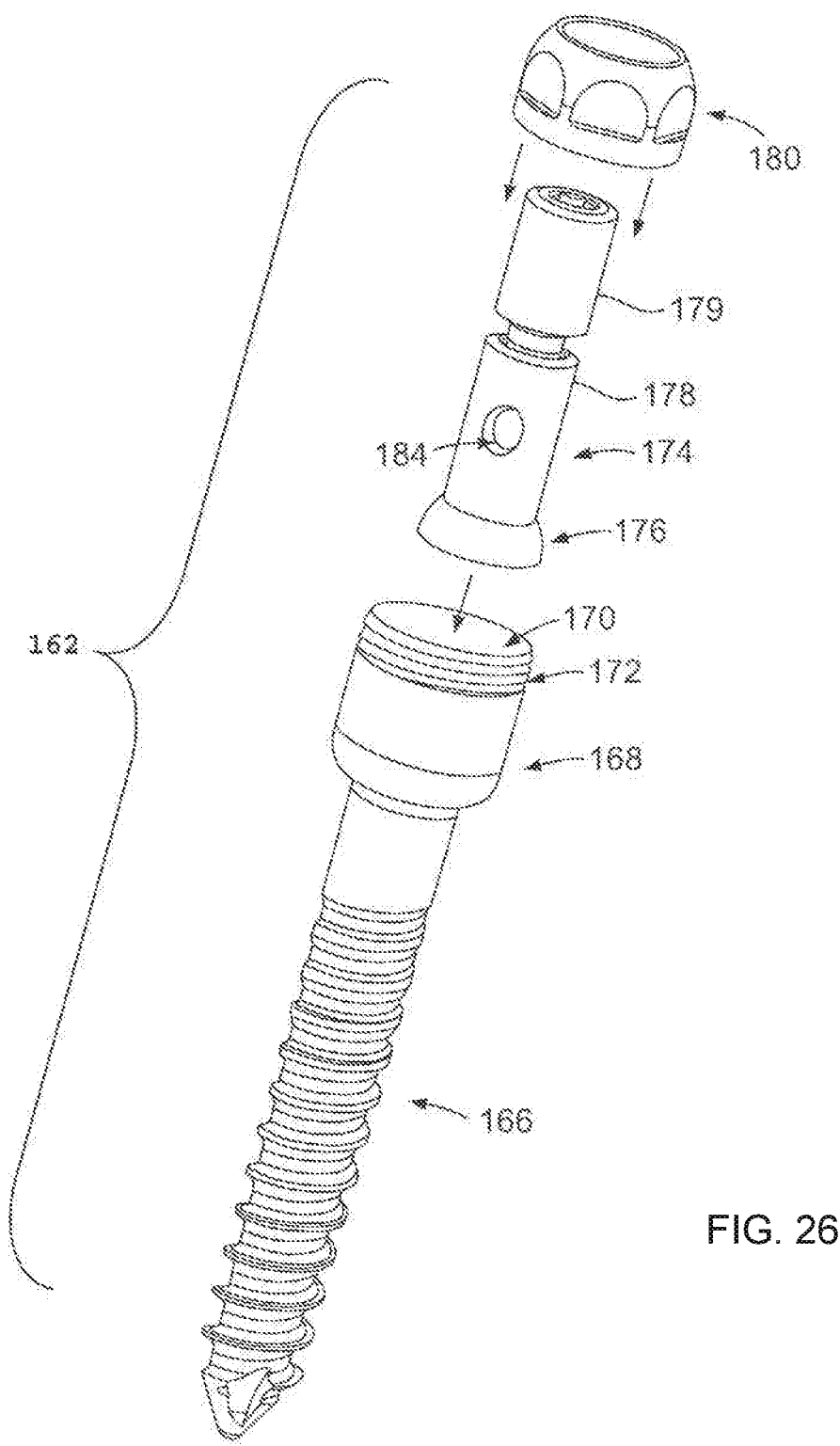
FIG. 26 is an exploded view of an anchor of FIG. 23 showing a nut for securing the post within a recess of the anchor base, a bore in the post for receiving a core member, and a groove in the post for receiving an end loop of an outer coil spring.

As best seen in FIG. 26, the post portion 178 includes a hollow or a bore 184 into which a portion 190 of the spanning structure 164 is received. Specifically, the portion 190 is a rod-like member linearly advanced through a bore 184 of a first anchor 162*a* and into a bore 184 of a second anchor 162*b*, representatively noted in FIG. 23. The post portion 178 receives a set screw 179 that may be driven into the post portion 178 to reach the bore 184 and apply pressure against the portion spanning structure rod 190.

The spanning structures 164 each include a first spring 194 and a second spring 196 located, sheath-like, around the rod portion 190. The first spring 194 has a smaller diameter than the second spring 196 so that the second spring 196 is also positioned, sheath-like, around the first spring 194. The first spring 194 is configured to be compressed from a natural position when the stabilization system 160 is loaded so that the anchors 162 between which the first spring 194 spans are moved toward each other. The second spring 196 is configured to be stretched or expanded from a natural position when the stabilization system 160 is loaded so that the anchors 162 are moved away from each other. In order to maintain the second spring 196 with the anchors 162, an end 198 of each second spring 196 includes an end loop 200 that may be secured around the post portion 178 and, in particular, in an annular groove (not shown) formed in the post portion 178.

As described above, one manner of selectively varying the stiffness of the second (expansion) spring 196 coil is by rotation of the ends 198 to enlarger or contract the diameter of the spring 196, thereby changing its spring equation. It should be noted that the size of the coils may be varied over the length of the spring 196 to give the spring non-linear spring/flexure characteristics. Similarly, the spring properties of the first (compression) spring 194 may be altered.

It should also be noted that the stabilization system 160 may also be adjusted through a small incision formed proximate an anchor 162 in a manner similar to that described for other forms herein. Removal of the rod portion 190 and release of one of the ends 198 of the second spring 196 allows the first spring 194 to be removed and changed, for instance, and the ends 198 may also be subsequently rotated and replaced on the post portion 178.

Figure 27:
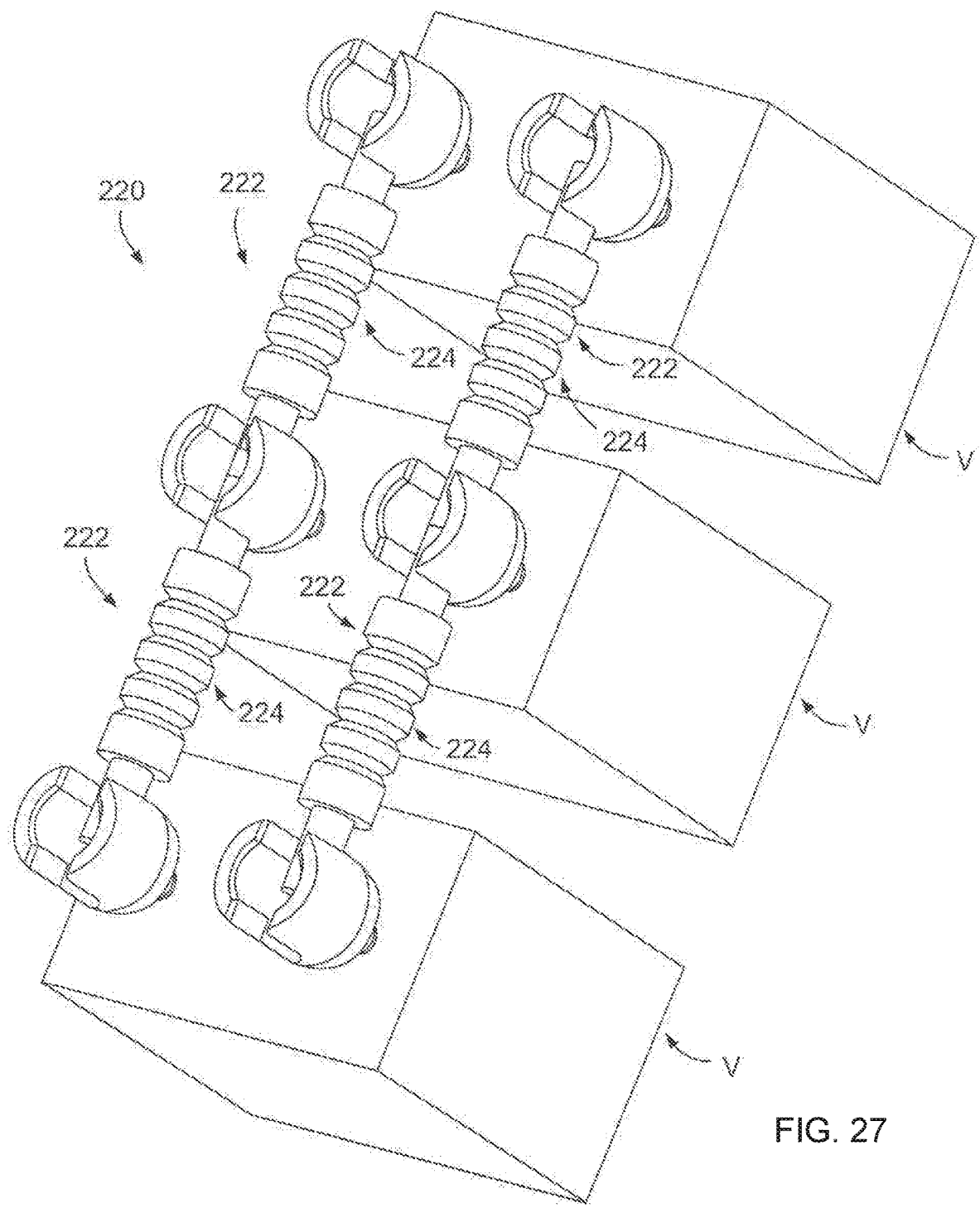
FIG. 27 is a perspective view of a stabilization system secured with representative adjacent vertebrae, the stabilization system including spanning structures having piston assemblies selectively pressurized with fluid such as gas.
Figure 28:
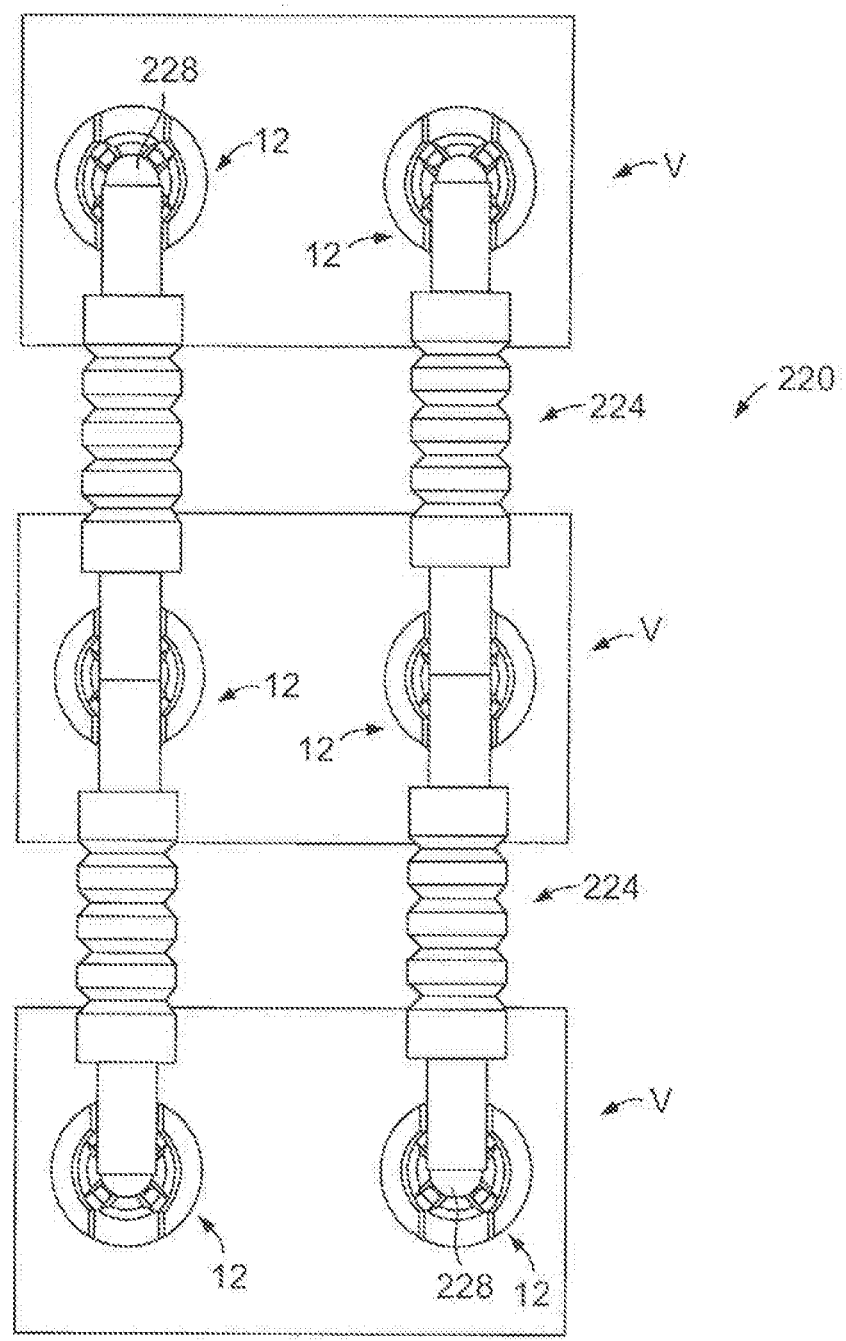
FIG. 28 is a top plan view of the stabilization system of FIG. 27.
Figure 29:
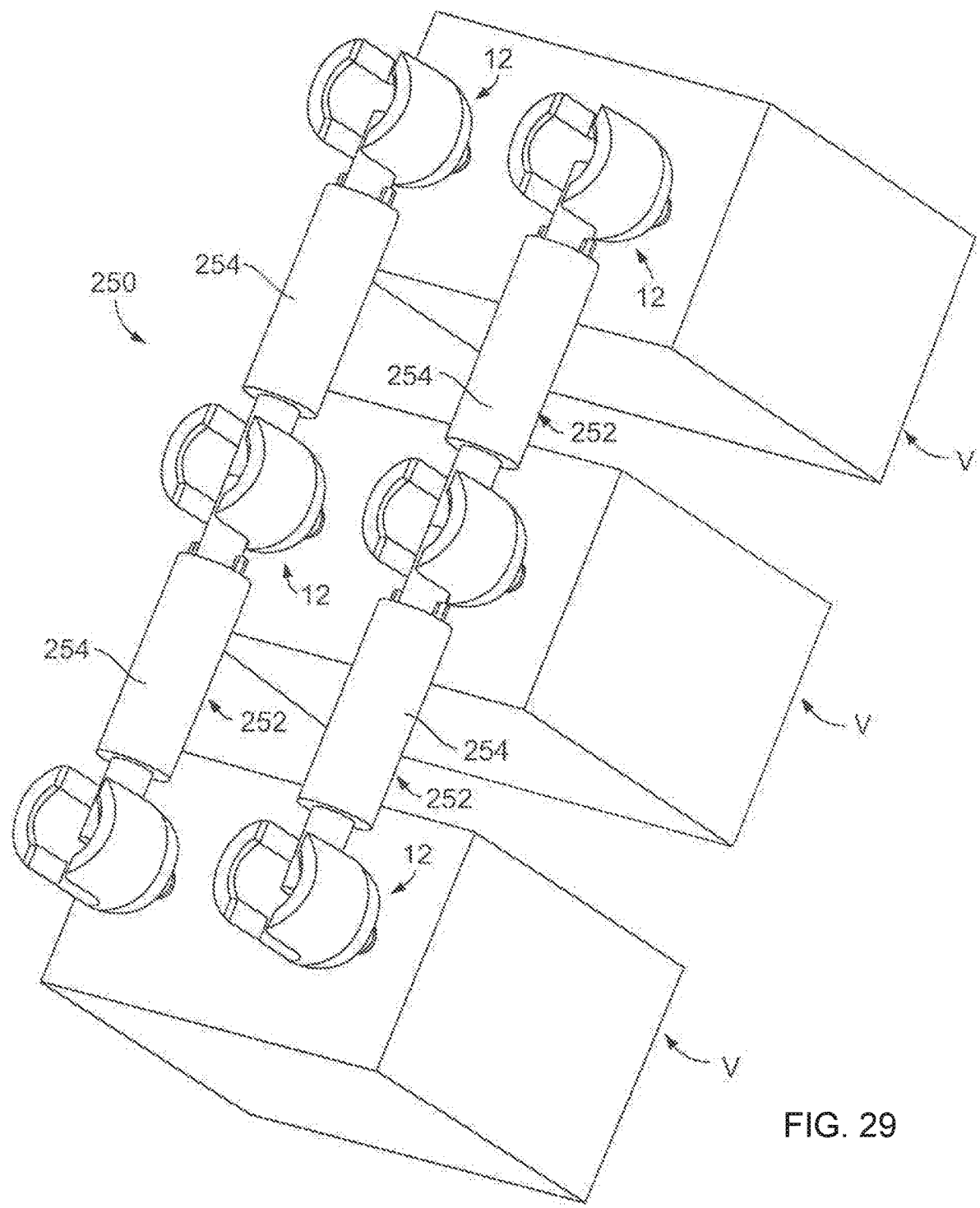
FIG. 29 is a perspective view of a stabilization system secured with representative adjacent vertebrae, the stabilization system including spanning structures having piston assemblies selectively filled with fluid such as liquid.
Figure 30:
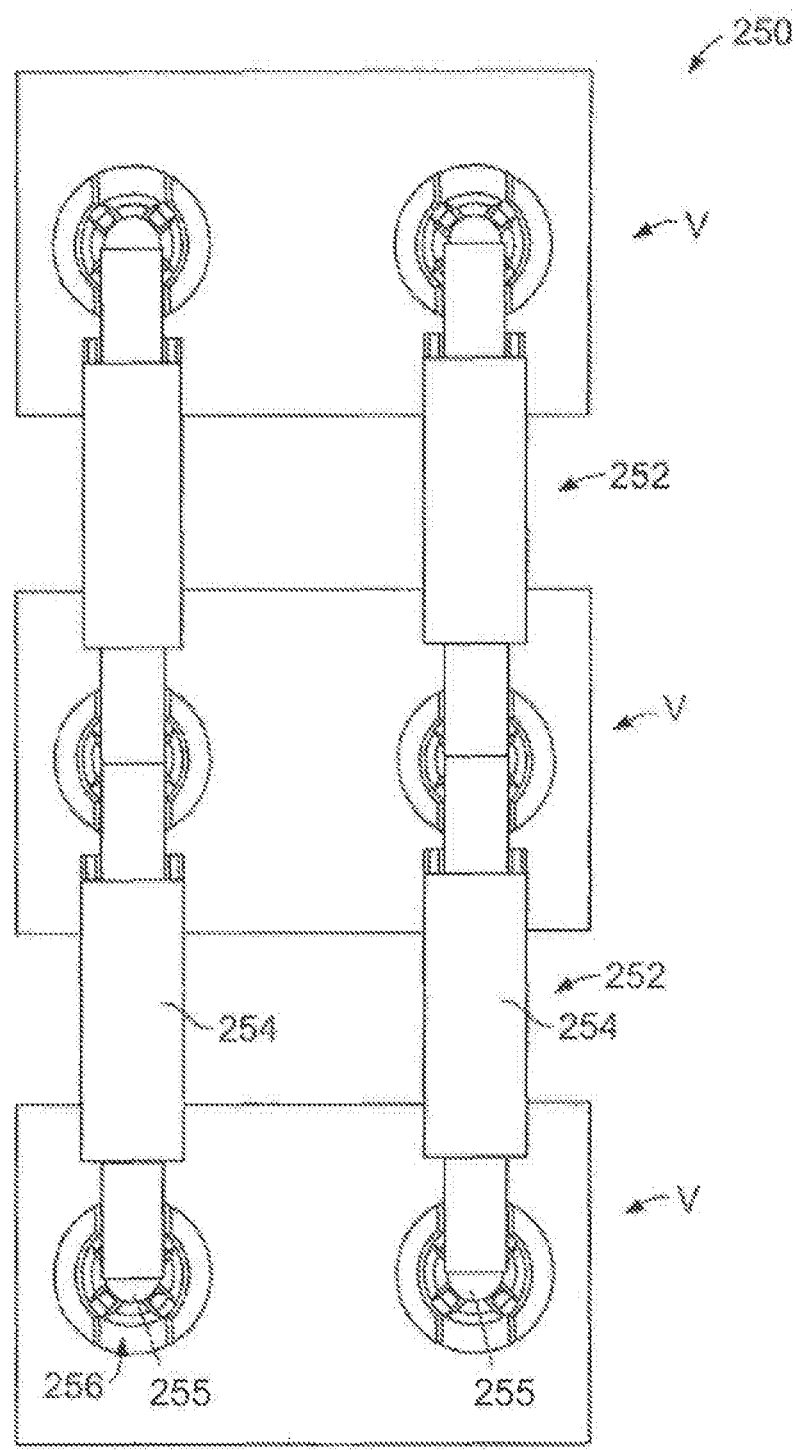
FIG. 30 is a top plan view of the stabilization system of FIG. 29.

Turning now to FIGS. 27-30, forms of spinal stabilization systems are shown using fluid and piston assemblies, fluid referring to both gasses and liquids. As will be discussed in greater detail below, a first form of such systems is shown in FIGS. 27 and 28 as stabilization system 220 having a plurality of anchors 12 and spanning structures 222, each having a gas-filled piston 224 assembly thereon. As will also be discussed below, FIGS. 29 and 30 depict a stabilization system 250 having a plurality of anchors 12 and spanning structures 252, each having a liquid filled piston assembly 254 thereon.

Turning to FIGS. 27 and 28, the piston assembly 224 may be referred to as a pneumatic assembly including a fluid chamber (not shown) and a piston head (not shown) reciprocable within the chamber. The fluid chamber is filled with gas so that movement of the piston head there within serves to either compress or expand the gas within the chamber. Accordingly, to some degree, the gas acts as a spring.

The "stiffness" of the gas acting like a spring can be modified by a surgeon user. In a preferred form, an end 226 of each piston assembly 224 includes a port 228 for connection with an external fluid reservoir (not shown) that allows a surgeon to pump in additional fluid or gas, or allows the surgeon to bleed off a portion of the gas. As in other embodiments discussed herein, such pressure adjustment may be performed post-operatively, such as through a small incision or via a hypodermic needle injection. Additionally, a reservoir may be implanted subcutaneously that allows for manual pumping of the reservoir, through the skin, and pressure relief. For instance, the reservoir may be a compressible bladder-type device connected via a one-way valve to inject fluid into the piston chamber, and a second one-way valve may be provided for reducing or bleeding fluid from the piston chamber into the bladder.

The stabilization system 220 may be implanted with little or no gas so that the bone-anchor interface is able to heal prior to loading of the stabilization system 220, as has also been discussed above, and subsequently the piston assembly 224 may be pressurized as desired. As can be seen, different piston assemblies 224 of the stabilization system 220 may be provided with different internal pressures within the piston chamber so that each piston assembly 224 has a selected "stiffness."

The stabilization system 250 of FIGS. 29 and 30 is similar in operation to that of FIGS. 27 and 28. The stabilization system 250 is a hydraulic system utilizing fluid in the form of a liquid that is incompressible or minimally compressible within piston assemblies 254. Accordingly, the piston assembly 254 is highly resistant to compression or expansion. While this may be viewed as a detriment, it is noted that pumping in or bleeding off of liquid from a port 255 located on an end 256 of the piston assembly 254 provides a high degree of predictability for the performance of the piston assembly 254. In increasing or decreasing the liquid volume, the distance between the anchors 12 to which the piston assembly 254 is secured is relatively easily determined by the surgeon; for instance, a surgeon may be using the stabilization system 250 to relieve pressure on a damaged intervertebral disc that is causing pressure and pain on the spinal column, and shifting of vertebrae away from each other by increasing the liquid volume in the piston assembly 254 is evident.

In a variation of the stabilization system 250, the piston assembly 254 may be provided with a dashpot damping structure (not shown) within the fluid (or, more appropriately within the liquid-filled fluid chamber of the piston assembly 254). In this manner, controlled and moderate compression or expansion of the piston assembly 254 is permitted, yet fast or sudden moves are resisted (in proportion to the square of the velocity, as is known in the art). In a further variation, the piston assembly 254 may be provided with an elastically compressible member or material (not shown), either externally located between the piston assembly 254 and an anchor 12 or internally within the piston fluid chamber. In still another variation, the piston assembly 254 may have a fluid of mixed phases, either of same or different material, so that the piston assembly 254 includes the compressibility of a gas form and the incompressibility of a liquid form, and the liquid and gas may be adjusted as desired.

As described, the piston assemblies 224 and 254 may be compressed only in their longitudinal directions, though they would have limited flexibility in other directions. Accordingly, the piston assemblies 224, 254 generally only permit flexure/compression in the anterior-posterior directions. The piston assemblies 224, 254 may be calibrated so as to select a desired amount of "stiffness" in their compression. If a compressible fluid were utilized, the "stiffness" may be variable (as opposed to linear based on Boyle's law). Additionally, the fluid may be a non-Newtonian fluid so that shear rate versus force is non-linear, or may have a damper effect by using a fluid of high viscosity and/or internal damper structure. The stiffness characteristics of different piston assemblies in the spinal stabilization systems may vary from assembly to assembly so that, for instance, the stiffness between two vertebral levels may have a first set of characteristics, while the stiffness between two other vertebral levels may have a second set of characteristics.

The above-noted reservoir may, alternatively, be located sub-cutaneously so that post-operative adjustment can be made without revision surgery. In some forms, separate valves may be provided on the piston assemblies for increasing pressure and for decreasing pressure. Additionally, the above-described keys or tools for adjusting the spanning structures or the mechanical performance characteristics thereof may also be joined with the spanning structures and implanted such that non-surgical adjustment of the keys or tools may be had via manipulation through the skin.

It should be noted that, as described, forms of the stabilization system described herein can be adjusted by a simple, relatively straightforward revision procedure, as described for the form of FIG. 6. The spanning portions described herein allow a continuous adjustment and selection (as opposed to an incremented selection based on rod diameter) of the stiffness or modulus of elasticity (or set of characteristics relating thereto). Additionally, spanning portions extending between an inferior vertebra and a second (medial) adjacent vertebra may have a first stiffness, while spanning portions extending between the medial vertebra and an adjacent superior vertebra may have a second stiffness or characteristics relating thereto.

Figure 31A:
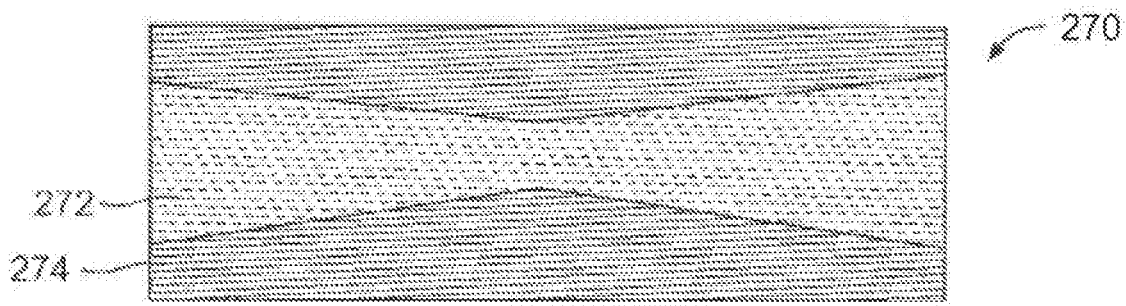
FIGS. 31A-31C are cross-sectional views of spanning structures for use in stabilization systems having varying spring and stiffness characteristics along their length.
Figure 31B:
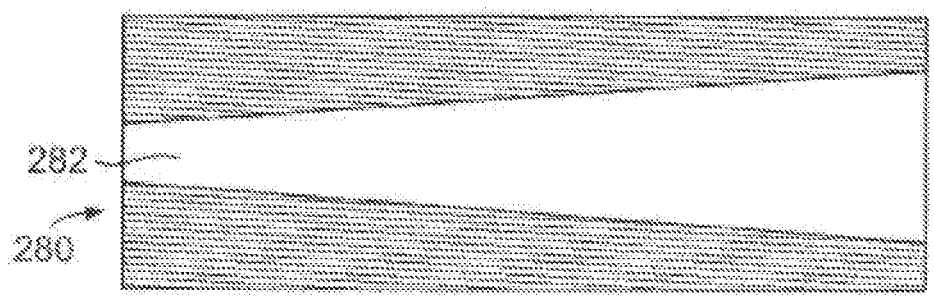
Figure 31C:
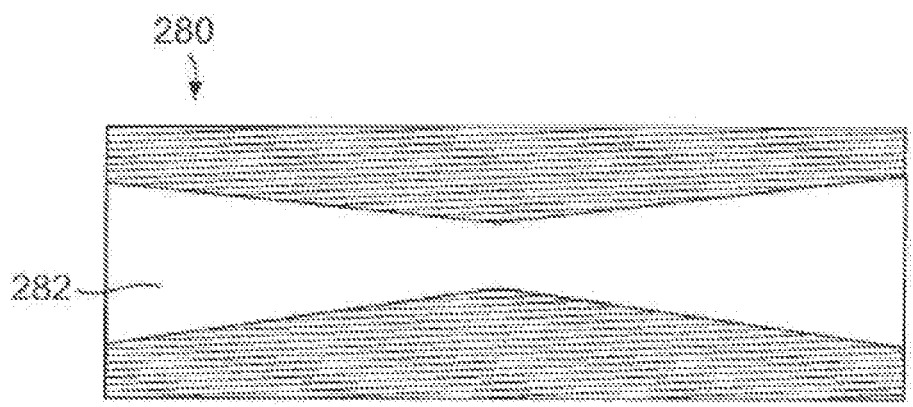

A variety of forms of spanning structures are illustrated in FIGS. 31A-31C. A spanning structure 270 may be constructed of various layers of material, two or more of which have differing linear moduli of elasticity. The thickness of the layers may be selected to impart a varying spring equation to the spanning structure 270 over its longitudinal length. For instance, a central core portion 272 may be formed of material with a first modulus of elasticity, and the central core portion may have a varying cross-sectional shape so that the spring equation for the core portion 272 varies over its longitudinal length. In order to maintain a constant outer diameter to the spanning structure 270, a layer 274 of constant outer diameter may be applied over the core portion, the layer 274 having a varying inner diameter corresponding to the outer diameter of the core portion 272. In this embodiment, the material of the layer portion 274 has an elastic modulus different from that of the core portion 272, and the materials and geometries of the core and layer (or layers) are selected to control or provide a specific set of flexure/bending characteristics.

In another form, a spanning structure 280 may have a hollow core or bore 282 of varying inner diameter. For instance, the bore 282 may have a conical shape (FIG. 22B), a double-frustum shape (FIG. 22C), or another shape. The varying inner diameter allows for the bending of the spanning structure 280 rod to be non-linear proportion to the force applied. In some forms, the above-described scalloping 32, 44 may be formed on the interior surface of the inner bore 282.

It should be noted that any of the above forms may be provided with shock absorbers or the like, such as at an interface between the spanning structures and the anchors. For instance, the spanning structures and the anchors may be joined by an elastomeric or polymeric coupling.

In variations of the present invention, the effective bending characteristics of spanning structures may be varied by varying their geometry, structure, and/or composition. For instance, a single (first) spanning portion may have a varying cross-section over its length, and/or the first spanning portion may have varying cross-section in comparison to a second spanning portion. In some forms, the spanning portions may be constructed as composite or layered member to impart desired flexure characteristics, including varying the thickness or size of layers so that the flexure characteristics are non-linear.

Additional benefits of the systems and methods described herein include improving device fixation, and/or preventing unwanted contact between devices and patient anatomy (e.g. the patient's spinal cord). The further use of methods described above, including the use of software analytics, may further aid in determining screw placement and orientation to achieve the ideal screw placement and/or rod shape. For example, the use of various apparatus described herein to achieve desired screw placement and orientation in turn provides improved alignment of a secondary device, such as a rod, with the screws heads. This benefit in turn allows the surgeon/user to achieve optimal sagittal and/or coronal alignment, which assists in rod placement and improves correction of the patient's anatomy.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and\or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

While the invention has been described with respect to specific examples including presently preferred modes of carrying out the invention, those skilled in the art will appreciate that there are numerous variations and permutations of the above described systems and techniques that fall within the spirit and scope of the invention.

What is claimed is:

1. A spinal stabilization system securable with a plurality of vertebrae, the system comprising:
   at least one anchor configured for attachment to at least two vertebrae;
   a plurality of spanning structures extending between and securable with the at least one anchor, each spanning structure having an adjustable bending stiffness;
   wherein the plurality of spanning structures are arranged in layers extending substantially the distance between the at least two vertebrae;
   wherein each of the spanning structures is adjusted to impart a different bending stiffness between its respective anchors;
   wherein the bending stiffness of each of the spanning structures is adjustable after being secured with the anchors;
   wherein the layers comprise an outer member of a first cross-sectional area and an inner portion of a second cross-sectional area that is larger than the first cross-sectional area; and
   wherein the outer member cross-sectional area is smaller than the inner portion cross-sectional area, the outer member and inner portion being configured to be positioned substantially within another structural member, the combined members being retained with a first end securable with a first vertebral body and a second end operatively fixable with a second vertebral body.

2. The system of claim 1, wherein the bending stiffness of each of the spanning structures is adjustable in an orientation corresponding to the orientation of the at least two vertebrae.

3. The system of claim 1, wherein the bending stiffness of each of the spanning structures is adjustable in anterior, posterior, lateral, and torsional modes.

4. The system of claim 1, wherein the bending stiffness of each of the spanning structures is variable in both longitudinal and transverse planes relative to the at least two vertebrae.

5. The system of claim 1, wherein the bending stiffness of each of the spanning structures is adjustable by selection of the material of the inner portion, and wherein the material of the inner portion is introducable after securing the outer member to the at least one anchor.

6. The system of claim 1, wherein the inner portion is comprised of a plurality of components, and wherein the bending stiffness of each of the spanning structures may also be adjusted by selecting a number of inner portion components disposed within the outer member.

7. The system of claim 6, wherein the bending stiffness of each of the spanning structures is adjustable by removal or addition of inner portion components.

8. The system of claim 1, wherein the bending stiffness of each of the spanning structures is adjustable by orientation of the inner portion relative to the outer member.

9. The system of claim 8, wherein at least one of the outer member and the inner portion has eccentrically positioned regions of reduced cross-sectional area,. wherein rotation of the regions provides a direction of decreased bending stiffness.

10. The system of claim 1, wherein the inner portion is at least one helical coil spring concentrically located inside the outer member comprised of at least one other helical coil spring.

11. The system of claim 10, wherein the bending stiffness of each of the spanning structures is also adjustable by adjusting at least one physical characteristic of the one or more helical coil springs.

12. The system of claim 11, wherein the at least one physical characteristic of the one or more helical coil springs includes at least one of the number of coils, the diameter of the coils, and the length of the spring.

13. The system of claim 10, wherein the one or more helical coil springs provide adjustable compression/expansion stiffness to the plurality of spanning structures.

14. The system of claim 10, wherein one of the helical coil springs provides a compression stiffness and the other helical coil spring provides an expansion stiffness to the plurality of spanning structures.

15. The system of claim 1, wherein the compression/expansion stiffness of the each spanning structure is selectively adjustable.

16. The system of claim 1, wherein the bending stiffness of each spanning structure is adjustable via a percutaneous incision in a patient's skin.

17. The system of claim 1, wherein at least one spanning structure of the plurality thereof is adjustable via an end thereof.

18. The system of claim 1, wherein at least one spanning structure of the plurality thereof is adjustable via an implanted key or tool without an incision.

* * * * *